(12) United States Patent
Yamashita et al.

(10) Patent No.: US 9,751,938 B2
(45) Date of Patent: *Sep. 5, 2017

(54) METHOD OF INHIBITING ACTIVATION OF A T CELL BY ADMINISTERING AN ANTI-RGM ANTIBODY OR AN RGM SIRNA

(71) Applicant: Mitsubishi Tanabe Pharma Corporation, Osaka-shi, Osaka (JP)

(72) Inventors: Toshihide Yamashita, Suita (JP); Takekazu Kubo, Chiba (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/149,314

(22) Filed: May 9, 2016

(65) Prior Publication Data

US 2016/0244517 A1 Aug. 25, 2016

Related U.S. Application Data

(62) Division of application No. 13/514,915, filed as application No. PCT/JP2010/071965 on Dec. 8, 2010, now Pat. No. 9,334,323.

(30) Foreign Application Priority Data

Dec. 9, 2009 (JP) ................. 2009-279189

(51) Int. Cl.
| | | |
|---|---|---|
| C07K 16/22 | (2006.01) | |
| A61K 31/07 | (2006.01) | |
| A61K 31/122 | (2006.01) | |
| A61K 31/355 | (2006.01) | |
| A61K 31/375 | (2006.01) | |
| A61K 33/00 | (2006.01) | |
| A61K 33/04 | (2006.01) | |
| A61K 33/06 | (2006.01) | |
| A61K 33/26 | (2006.01) | |
| A61K 33/30 | (2006.01) | |
| C07K 16/18 | (2006.01) | |
| C07K 16/28 | (2006.01) | |
| C12N 15/113 | (2010.01) | |
| A61K 39/00 | (2006.01) | |

(52) U.S. Cl.
CPC ............. *C07K 16/22* (2013.01); *A61K 31/07* (2013.01); *A61K 31/122* (2013.01); *A61K 31/355* (2013.01); *A61K 31/375* (2013.01); *A61K 33/00* (2013.01); *A61K 33/04* (2013.01); *A61K 33/06* (2013.01); *A61K 33/26* (2013.01); *A61K 33/30* (2013.01); *C07K 16/18* (2013.01); *C07K 16/28* (2013.01); *C12N 15/1136* (2013.01); *A61K 2039/505* (2013.01); *C07K 2317/76* (2013.01); *C12N 2310/14* (2013.01); *C12N 2320/30* (2013.01)

(58) Field of Classification Search
CPC ................................ A61K 39/00; A61K 48/00
See application file for complete search history.

(56) References Cited

U.S. PATENT DOCUMENTS

| | | |
|---|---|---|
| 2007/0253946 A1 | 11/2007 | Yamashita et al. |
| 2009/0297527 A1 | 12/2009 | Muller et al. |
| 2009/0325934 A1 | 12/2009 | Navratil et al. |
| 2010/0028340 A1 | 2/2010 | Mueller et al. |
| 2013/0101605 A1 | 4/2013 | Strittmatter et al. |

FOREIGN PATENT DOCUMENTS

| | | |
|---|---|---|
| JP | 2009-279189 A | 6/2011 |
| WO | WO 00/56772 A1 | 9/2000 |
| WO | WO 02/051438 A2 | 7/2002 |
| WO | WO 2005/087268 A1 | 9/2005 |
| WO | WO 2007/039256 A2 | 4/2007 |
| WO | WO 2009/030500 A1 | 3/2009 |
| WO | WO 2009/106356 A1 | 9/2009 |
| WO | WO 2015/120138 A2 | 8/2015 |

OTHER PUBLICATIONS

Guo-Lan, Wan (editor), "Modern Practical Childhood Neuropathology," Zhengzhou University Press (Jul. 2008), pp. 152-153.
Kubo et al., *J. Neuroimmune Pharmacol.*, 7: 524-528 (2012).
Minohara et al., "Amelioration of experimental autoimmune encephalomyelitis by Rho Kinase Inhibitor," *Journal of Neurological Sciences*, 238(supplement 1): S238, Poster Abstract 0548 (Nov. 8, 2005).
National Center for Biotechnology Information, NCBI webpage printout reciting classification of the isoforms of RGM and information about multiple sclerosis (retrieved and printed on Oct. 10, 2014).
Nohra et al., *Genes Immun.*, 11(4): 279-293 (2010).
Yusuf-Makagiansar et al., *Medical Research Reviews*, 22(2): 146-167 (2002).
European Patent Office, Extended European Search Report in European Patent Application No. 10835979.5 (Apr. 3, 2013).

(Continued)

*Primary Examiner* — Prema Mertz
(74) *Attorney, Agent, or Firm* — Leydig, Voit & Mayer, Ltd.

(57) ABSTRACT

Provided is a T cell activation inhibitor containing an RGM inhibiting substance such as an anti-RGM neutralizing antibody and the like as an active ingredient. The T cell activation inhibitor is useful as a pharmaceutical composition for the prophylaxis or treatment of autoimmune diseases such as multiple sclerosis and the like, and other diseases caused by T cell activation. In addition, a T cell activation inhibiting substance can be screened for by contacting a test substance with RGM and selecting a test substance that lowers the activity level of RGM.

20 Claims, 12 Drawing Sheets

(56) References Cited

OTHER PUBLICATIONS

Japanese Patent Office, International Search Report in International Patent Application No. PCT/JP2010/071965 (Feb. 8, 2011).
International Bureau of WIPO, International Preliminary Report on Patentability in International Patent Application No. PCT/JP2010/071965 (Dec. 22, 2011).
Ara et al., *Journal of Neuroscience Research*, 86: 125-135 (2008).
London et al., *Nat. Rev. Neurol.*, 9: 44-53 (20123).
Mueller et al., *Phil. Trans. R. Soc. B.*, 361: 1513-1529 (2006).
Yamashita et al., *Current Opinion in Neurobiology*, 17: 29-34 (2007).

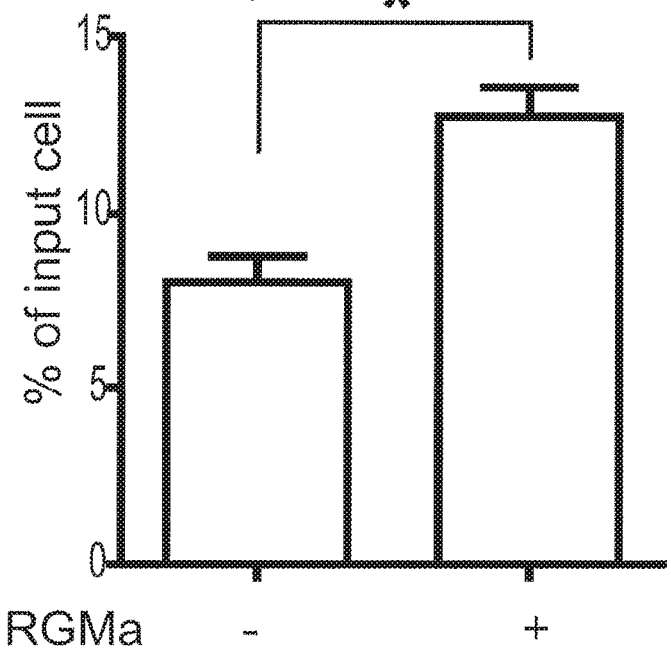

SEQUENCE LISTING

```
<160> NUMBER OF SEQ ID NOS: 8

<210> SEQ ID NO 1
<211> LENGTH: 1299
<212> TYPE: DNA
<213> ORGANISM: Homo sapiens

<400> SEQUENCE: 1
atggggagag gggcaggacg ttcagccctg ggattctggc cgaccctcgc cttccttctc      60
tgcagcttcc ccgcagccac ctccccgtgc aagatcctca agtgcaactc tgagttctgg    120
agcgccacgt cgggcagcca cgccccagcc tcagacgaca ccccgagtt ctgtgcagcc     180 ttgcgcagct acgccctgtg cacgcggcgg acggcccgca cctgccgggg tgacctggcc    240
taccactcgg ccgtccatgg catagaggac ctcatgagcc agcacaactg ctccaaggat    300
ggccccacct cgcagccacg cctgcgcacg ctcccaccgg ccggagacag ccaggagcgc    360
tcggacagcc ccgagatctg ccattacgag aagagctttc acaagcactc ggccacccc    420 aactacacgc actgtggcct cttcgggac ccacacctca ggactttcac cgaccgcttc     480
cagacctgca aggtgcaggg cgcctggccg ctcatcgaca taattacct gaacgtgcag    540 gtcaccaaca cgcctgtgct gccccggctca gcggccactg ccaccagcaa gctcaccatc    600
atcttcaaga acttccagga gtgtgtggac cagaaggtgt accaggctga gatggacgag   660
ctcccggccg ccttcgtgga tggctctaag aacggtgggg acaagcacgg ggccaacagc   720
ctgaagatca ctgagaaggt gtcaggccag cacgtggaga tccaggccaa gtacatcggc   780
accaccatcg tggtgcgcca ggtgggccgc tacctgacct ttgccgtccg catgccagag   840
gaagtggtca atgctgtgga ggactgggac agccagggtc tctacctctg cctgcggggc   900
tgccccctca accagcagat cgacttccag gccttccaca ccaatgctga gggcaccggt   960
gcccgcaggc tggcagccgc cagccctgca cccacagccc ccgagacctt cccatacgag  1020
acagccgtgg ccaagtgcaa ggagaagctg ccggtggagg acctgtacta ccaggcctgc  1080
gtcttcgacc tcctcaccac gggcgacgtg aacttcacac tggccgccta ctacgcgttg  1140
gaggatgtca agatgctcca ctccaacaaa gacaaactgc acctgtatga gaggactcgg  1200
gacctgccag gcagggcggc tgcggggctg ccccctggcc ccggccct cctgggcgcc  1260 ctcgtcccgc tcctggccct gctccctgtg ttctgctag                           1299

<210> SEQ ID NO 2
<211> LENGTH: 432
<212> TYPE: PRT
```

-continued

<213> ORGANISM: Homo sapiens

<400> SEQUENCE: 2

```
Met Gly Arg Gly Ala Gly Arg Ser Ala Leu Gly Phe Trp Pro Thr Leu
1               5                   10                  15
Ala Phe Leu Leu Cys Ser Phe Pro Ala Ala Thr Ser Pro Cys Lys Ile
            20                  25                  30
Leu Lys Cys Asn Ser Glu Phe Trp Ser Ala Thr Ser Gly Ser His Ala
        35                  40                  45
Pro Ala Ser Asp Asp Thr Pro Glu Phe Cys Ala Ala Leu Arg Ser Tyr
    50                  55                  60
Ala Leu Cys Thr Arg Arg Thr Ala Arg Thr Cys Arg Gly Asp Leu Ala
65                  70                  75                  80
Tyr His Ser Ala Val His Gly Ile Glu Asp Leu Met Ser Gln His Asn
                85                  90                  95
Cys Ser Lys Asp Gly Pro Thr Ser Gln Pro Arg Leu Arg Thr Leu Pro
            100                 105                 110
Pro Ala Gly Asp Ser Gln Glu Arg Ser Asp Ser Pro Glu Ile Cys His
        115                 120                 125
Tyr Glu Lys Ser Phe His Lys His Ser Ala Thr Pro Asn Tyr Thr His
    130                 135                 140
Cys Gly Leu Phe Gly Asp Pro His Leu Arg Thr Phe Thr Asp Arg Phe
145                 150                 155                 160
Gln Thr Cys Lys Val Gln Gly Ala Trp Pro Leu Ile Asp Asn Asn Tyr
                165                 170                 175
Leu Asn Val Gln Val Thr Asn Thr Pro Val Leu Pro Gly Ser Ala Ala
            180                 185                 190
Thr Ala Thr Ser Lys Leu Thr Ile Ile Phe Lys Asn Phe Gln Glu Cys
        195                 200                 205
Val Asp Gln Lys Val Tyr Gln Ala Glu Met Asp Glu Leu Pro Ala Ala
    210                 215                 220
Phe Val Asp Gly Ser Lys Asn Gly Gly Asp Lys His Gly Ala Asn Ser
225                 230                 235                 240
Leu Lys Ile Thr Glu Lys Val Ser Gly Gln His Val Glu Ile Gln Ala
                245                 250                 255
Lys Tyr Ile Gly Thr Thr Ile Val Val Arg Gln Val Gly Arg Tyr Leu
            260                 265                 270
Thr Phe Ala Val Arg Met Pro Glu Glu Val Val Asn Ala Val Glu Asp
        275                 280                 285
Trp Asp Ser Gln Gly Leu Tyr Leu Cys Leu Arg Gly Cys Pro Leu Asn
    290                 295                 300
Gln Gln Ile Asp Phe Gln Ala Phe His Thr Asn Ala Glu Gly Thr Gly
305                 310                 315                 320
Ala Arg Arg Leu Ala Ala Ala Ser Pro Ala Pro Thr Ala Pro Glu Thr
                325                 330                 335
Phe Pro Tyr Glu Thr Ala Val Ala Lys Cys Lys Glu Lys Leu Pro Val
            340                 345                 350
Glu Asp Leu Tyr Tyr Gln Ala Cys Val Phe Asp Leu Leu Thr Thr Gly
        355                 360                 365
Asp Val Asn Phe Thr Leu Ala Ala Tyr Tyr Ala Leu Glu Asp Val Lys
    370                 375                 380
Met Leu His Ser Asn Lys Asp Lys Leu His Leu Tyr Glu Arg Thr Arg
385                 390                 395                 400
```

Asp Leu Pro Gly Arg Ala Ala Ala Gly Leu Pro Leu Ala Pro Arg Pro
            405                 410                 415

Leu Leu Gly Ala Leu Val Pro Leu Leu Ala Leu Leu Pro Val Phe Cys
        420                 425                 430

<210> SEQ ID NO 3
<211> LENGTH: 1296
<212> TYPE: DNA
<213> ORGANISM: Rattus norvegicus

<400> SEQUENCE: 3

| | | | | | |
|---|---|---|---|---|---|
| atggggagag | gggcaggacg | ttcagccctg | ggattgtggc | cgaccctcgc | cttccttctc | 60 |
| tgcagctttc | ccgcagctat | ctctccctgc | aagatcctca | agtgcaactc | tgagttctgg | 120 |
| agcgccacgt | cgtcaggcag | ccacgcccct | gcctctgacg | acgtgcccga | gttctgtgct | 180 |
| gccctgcgca | cctacgccct | gtgcacgcga | cggacagccc | gcacctgccg | gggcgacctg | 240 |
| gcttaccact | cggctgtcca | tggcatagag | gacctcatga | gccagcacaa | ctgctccaag | 300 |
| gatggcccca | cctcacagcc | tcgagtgcgc | acgctcccgc | cagctgggga | cagccaggag | 360 |
| cgctcagata | gccccgagat | ctgccactat | gagaagagtt | ccacaagca | ctcagctgcc | 420 |
| cccaactaca | ctcactgcgg | cctctttggg | acccacacc | tcaggacttt | cacagaccac | 480 |
| ttccagacat | gtaaggtgca | aggcgcttgg | cctctcatcg | acaataatta | cctgaacgtg | 540 |
| caggtcacca | atacacctgt | gctgcccggc | tctgccgcca | ctgccaccag | caagctcacc | 600 |
| atcatcttca | gaacttcca | agagtgtgtg | gaccagaaag | tataccaagc | cgagatggac | 660 |
| gagcttccgt | ccgccttgc | cgatggctcc | aaaaacggtg | gagataaaca | cggagccaac | 720 |
| agcctgaaga | tcacagagaa | ggtgtcaggc | cagcacgtgg | agatccaggc | caagtacatc | 780 |
| ggcaccacca | tcgtggtgag | acaggtgggc | cgctacctga | ccttcgccgt | ccggatgccc | 840 |
| gaggaggtag | tcaacgccgt | ggaggaccgt | gacagccaag | gcctctacct | ctgcctgcgg | 900 |
| ggctgcccgc | tcaaccagca | gatcgacttc | caggcttcc | gtgccaacgc | cgagagccct | 960 |
| cgcaggccag | cagctgccag | cccctctcct | gtggtccccg | agacatttcc | gtacgagaca | 1020 |
| gctgtggcca | agtgcaaaga | gaagctgcct | gtagaagact | tgtactacca | ggcctgtgtc | 1080 |
| ttcgacctcc | tcacgactgg | cgacgtgaac | ttcacgctgg | ccgcctacta | tgctttggag | 1140 |
| gatggcaaga | tgctccactc | caacaaggac | aagctacacc | tgtttgaaag | gactcgggag | 1200 |
| ctgcctggcg | ctgtggccgc | tgcagcattt | cccttggccc | ccgagatgct | cccgggcacc | 1260 |
| gtcacacttc | tggtcctgct | gcctctgttc | tggtag | | | 1296 |

<210> SEQ ID NO 4
<211> LENGTH: 431
<212> TYPE: PRT
<213> ORGANISM: Rattus norvegicus

<400> SEQUENCE: 4

Met Gly Arg Gly Ala Gly Arg Ser Ala Leu Gly Leu Trp Pro Thr Leu
1               5                   10                  15

Ala Phe Leu Leu Cys Ser Phe Pro Ala Ala Ile Ser Pro Cys Lys Ile
            20                  25                  30

Leu Lys Cys Asn Ser Glu Phe Trp Ser Ala Thr Ser Ser Gly Ser His
        35                  40                  45

Ala Pro Ala Ser Asp Asp Val Pro Glu Phe Cys Ala Ala Leu Arg Thr
    50                  55                  60

Tyr Ala Leu Cys Thr Arg Arg Thr Ala Arg Thr Cys Arg Gly Asp Leu

```
                65                  70                  75                  80
        Ala Tyr His Ser Ala Val His Gly Ile Glu Asp Leu Met Ser Gln His
                            85                  90                  95

Asn Cys Ser Lys Asp Gly Pro Thr Ser Gln Pro Arg Val Arg Thr Leu
                        100                 105                 110

Pro Pro Ala Gly Asp Ser Gln Glu Arg Ser Asp Ser Pro Glu Ile Cys
                    115                 120                 125

His Tyr Glu Lys Ser Phe His Lys His Ser Ala Ala Pro Asn Tyr Thr
                130                 135                 140

His Cys Gly Leu Phe Gly Asp Pro His Leu Arg Thr Phe Thr Asp His
        145                 150                 155                 160

Phe Gln Thr Cys Lys Val Gln Gly Ala Trp Pro Leu Ile Asp Asn Asn
                        165                 170                 175

Tyr Leu Asn Val Gln Val Thr Asn Thr Pro Val Leu Pro Gly Ser Ala
                    180                 185                 190

Ala Thr Ala Thr Ser Lys Leu Thr Ile Ile Phe Lys Asn Phe Gln Glu
                195                 200                 205

Cys Val Asp Gln Lys Val Tyr Gln Ala Glu Met Asp Glu Leu Pro Ser
                210                 215                 220

Ala Phe Ala Asp Gly Ser Lys Asn Gly Gly Asp Lys His Gly Ala Asn
        225                 230                 235                 240

Ser Leu Lys Ile Thr Glu Lys Val Ser Gly Gln His Val Glu Ile Gln
                        245                 250                 255

Ala Lys Tyr Ile Gly Thr Thr Ile Val Val Arg Gln Val Gly Arg Tyr
                    260                 265                 270

Leu Thr Phe Ala Val Arg Met Pro Glu Glu Val Val Asn Ala Val Glu
                275                 280                 285

Asp Arg Asp Ser Gln Gly Leu Tyr Leu Cys Leu Arg Gly Cys Pro Leu
                290                 295                 300

Asn Gln Gln Ile Asp Phe Gln Ala Phe Arg Ala Asn Ala Glu Ser Pro
        305                 310                 315                 320

Arg Arg Pro Ala Ala Ala Ser Pro Ser Pro Val Val Pro Glu Thr Phe
                        325                 330                 335

Pro Tyr Glu Thr Ala Val Ala Lys Cys Lys Glu Lys Leu Pro Val Glu
                    340                 345                 350

Asp Leu Tyr Tyr Gln Ala Cys Val Phe Asp Leu Leu Thr Thr Gly Asp
                355                 360                 365

Val Asn Phe Thr Leu Ala Ala Tyr Tyr Ala Leu Glu Asp Gly Lys Met
                370                 375                 380

Leu His Ser Asn Lys Asp Lys Leu His Leu Phe Glu Arg Thr Arg Glu
        385                 390                 395                 400

Leu Pro Gly Ala Val Ala Ala Ala Phe Pro Leu Ala Pro Glu Met
                        405                 410                 415

Leu Pro Gly Thr Val Thr Leu Leu Val Leu Leu Pro Leu Phe Trp
                    420                 425                 430

<210> SEQ ID NO 5
<211> LENGTH: 21
<212> TYPE: PRT
<213> ORGANISM: Artificial Sequence
<220> FEATURE:
<223> OTHER INFORMATION: Synthetic Fragment of MOG

<400> SEQUENCE: 5

Met Glu Val Gly Trp Tyr Arg Ser Pro Phe Ser Arg Val Val His Leu
```

```
                1               5                      10                     15
Tyr Arg Asn Gly Lys
                                20

<210> SEQ ID NO 6
<211> LENGTH: 13
<212> TYPE: PRT
<213> ORGANISM: Artificial Sequence
<220> FEATURE:
<223> OTHER INFORMATION: Synthetic Fragment of PLP

<400> SEQUENCE: 6

His Ser Leu Gly Lys Trp Leu Gly His Pro Asp Lys Phe
1               5                      10

<210> SEQ ID NO 7
<211> LENGTH: 25
<212> TYPE: RNA
<213> ORGANISM: Artificial Sequence
<220> FEATURE:
<223> OTHER INFORMATION: Synthetic Sense strands of mouse RGMa siRNA

<400> SEQUENCE: 7
aaagaggccg cagugagugu aguug                                                    25

<210> SEQ ID NO 8
<211> LENGTH: 25
<212> TYPE: RNA
<213> ORGANISM: Artificial Sequence
<220> FEATURE:
<223> OTHER INFORMATION: Synthetic Antisense strands of mouse RGMa siRNA

<400> SEQUENCE: 8
caacuacacu cacugcggcc ucuuu                                                    25
```

METHOD OF INHIBITING ACTIVATION OF A T CELL BY ADMINISTERING AN ANTI-RGM ANTIBODY OR AN RGM SIRNA

CROSS-REFERENCE TO RELATED APPLICATIONS

This patent application is a divisional of copending U.S. patent application Ser. No. 13/514,915, filed on Aug. 10, 2012, which is the U.S. national phase of International Patent Application No. PCT/JP2010/071965, filed Dec. 8, 2010, which claims the benefit of Japanese Patent Application No. 2009/279189, filed Dec. 9, 2009, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 12,398 bytes ASCII (Text) file named "723569Sequence-Listing.txt," created Apr. 18, 2016.

TECHNICAL FIELD

The present invention relates to a T cell activation inhibitor, a pharmaceutical composition comprising same and a screening method for a T cell activation inhibiting substance. More particularly, the present invention relates to a T cell activation inhibitor comprising an RGM inhibiting substance as an active ingredient, a pharmaceutical composition for the prophylaxis or treatment of a disease caused by T cell activation, which comprises the T cell activation inhibitor, and a method for screening for a T cell activation inhibiting substance, comprising a step of contacting a test substance with RGM.

BACKGROUND ART

RGM (repulsive guidance molecule) is a membrane protein initially identified as an axon inducing molecule in the visual system (see non-patent document 1). The RGM family includes 3 kinds of members called RGMa, RGMb and RGMc, and at least RGMa and RGMb are known to act through the same signal transduction mechanism (see non-patent document 2). Subsequent studies have clarified that RGM has a function of axon induction and lamina formation in *Xenopus* and chicken embryos, as well as a function of regulating head neural tube closure and the like in a mouse embryo (see non-patent document 3). In addition to the functions in the developmental stages, RGM is reexpressed after damage on the central nervous system in adult human and rat, and inhibition of RGM enhances growth of axon after spinal damage and promotes functional recovery in rats (see non-patent document 4). Therefore, RGM is considered as a substance inhibiting axon regeneration after damage on the central nervous system. Also, patent document 1 discloses an axon regeneration promoter comprising an anti-RGM neutralizing antibody as an active ingredient.

Multiple sclerosis is a chronic disease wherein myelin (myelin sheath) covering nerve fibers in the brain and the spinal cord is inflamed to cause demyelination, which prevents smooth transmission of neural information, thereby provoking various symptoms such as visual disorder, movement disorder, hypesthesia, disequilibrium and the like. The etiology has not been clarified as yet, and the disease cannot be completely cured by the current medicine. While it is recognized as one of the autoimmune diseases, the detail of the onset mechanism thereof has not been elucidated. For example, non-patent document 5 reports that $CD4^+$ T cells immunologically attack myelin and oligodendrocyte in the white matter of the brain and the spinal cord.

DOCUMENT LIST

Patent Document patent document 1: JP-B-3981148

Non-Patent Documents non-patent document 1: Stahl, B., Muller, B., von Boxberg, Y., Cox, E. C. & Bonhoeffer, F. Biochemical characterization of a putative axonal guidance molecule of the chick visual system. Neuron 5, 735-743 (1990)

non-patent document 2: Liu, X., Hashimoto, M., Horii, H., Yamaguchi, A., Naito, K. and Yamashita, T. Repulsive guidance molecule b inhibits neurite growth and is increased after spinal cord injury. Biochem. Biophys. Res. Commun. 382, 795-800 (2009)

non-patent document 3: Yamashita, T., Mueller, B. K. & Hata, K. Neogenin and repulsive guidance molecule signaling in the central nervous system. Curr. Opin. Neurobiol. 17, 29-34 (2007)

non-patent document 4: Hata, K. et al. RGMa inhibition promotes axonal growth and recovery after spinal cord injury. J. Cell Biol. 173, 47-58 (2006)

non-patent document 5: Trapp, B. D., Ransohoff, R. M., Fisher, E. & Rudick, R. Neurodegeneration in multiple sclerosis: relationship to neurological disability. Neuroscientist 5, 48-57 (1999)

SUMMARY OF THE INVENTION

Problems to be Solved by the Invention

The present invention aims to find a novel function of RGM, and provide a novel T cell activation inhibitor, a pharmaceutical composition for the prophylaxis or treatment of a disease caused by T cell activation, and a screening method for a T cell activation inhibiting substance.

Means of Solving the Problems

The present invention encompasses each of the following inventions to solve the above-mentioned problems.
[1] A T cell activation inhibitor comprising an RGM inhibiting substance as an active ingredient.
[2] The T cell activation inhibitor of the aforementioned [1], wherein the RGM inhibiting substance is an anti-RGM neutralizing antibody.
[3] The T cell activation inhibitor of the aforementioned [1], wherein the RGM inhibiting substance is RGM siRNA.
[4] A pharmaceutical composition for the prophylaxis or treatment of a disease caused by T cell activation, comprising the T cell activation inhibitor of any of the aforementioned [1]-[3].
[5] The pharmaceutical composition of the aforementioned [4], wherein the disease caused by T cell activation is an autoimmune disease. [6] The pharmaceutical composition of the aforementioned [5], wherein the autoimmune disease is multiple sclerosis.

[7] A method of screening for a T cell activation inhibiting substance, comprising a step of contacting a test substance with RGM, a step of measuring the activity level of the aforementioned RGM, a step of comparing the aforementioned activity level with that of RGM free of contact with a test substance, and a step of selecting a test substance that reduces the activity level of RGM.
[8] A method of inhibiting activation of T cell, comprising a step of contacting an RGM inhibiting substance with an RGM expressing cell.
[9] The method of inhibiting activation of T cell of the aforementioned [8], wherein the RGM inhibiting substance is an anti-RGM neutralizing antibody.
[10] The method of inhibiting activation of T cell of the aforementioned [8], wherein the RGM inhibiting substance is an RGM siRNA.
[11] A method of preventing or treating an autoimmune disease, comprising administering an effective amount of the T cell activation inhibitor of any of the aforementioned [1]-[3] to a mammal.
[12] Use of the T cell activation inhibitor of any of the aforementioned [1]-[3], for the production of a pharmaceutical composition for the prophylaxis or treatment of an autoimmune disease.
[13] The T cell activation inhibitor of any of the aforementioned [1]-[3] for use in the prophylaxis or treatment of an autoimmune disease.

Effect of the Invention

The present invention can provide a novel T cell activation inhibitor. The T cell activation inhibitor is useful for the prophylaxis or treatment of a disease caused by T cell activation, for example, an autoimmune disease. In addition, a T cell activation inhibiting substance obtainable by the screening method of the present invention serves as a candidate active ingredient of a prophylactic or therapeutic drug for a disease caused by T cell activation.

BRIEF DESCRIPTION OF THE DRAWINGS

FIG. 5(A) shows the results of measuring adhesion ratio of splenocytes to fibronectin in the presence or absence of stimulation with RGMa.

DESCRIPTION OF EMBODIMENTS

Figure 1:
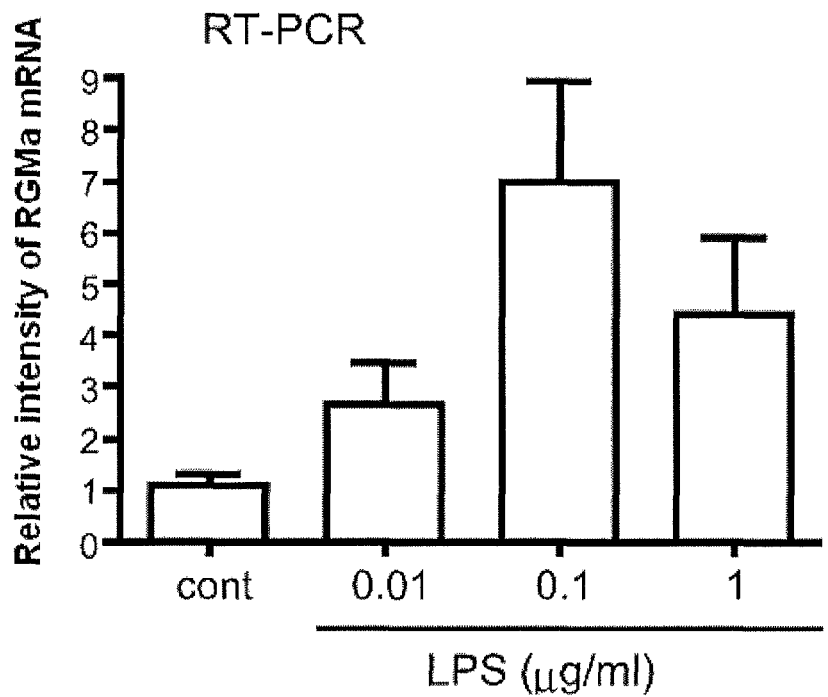
FIG. 1 shows the results of measuring the expression of RGMa mRNA in bone marrow-derived dendritic cells (BMDCs) stimulated with LPS, by real-time quantitative PCR.

The present inventors have found for the first time that RGM is expressed in bone marrow-derived dendritic cells (BMDCs) and RGM receptor is expressed on CD4$^+$ T cell and CD11b$^+$ macrophage, and that Rap1 is activated when RGM binds to RGMa receptor on CD4$^+$ T cell and CD11b$^+$ macrophage, thereby potentiating the cell adhesion activity of CD4$^+$ T cell or CD11b$^+$ macrophage. The present inventors have clarified in an experiment using a multiple sclerosis model mouse that administration of an anti-RGM neutralizing antibody reduces both the clinical symptoms and the tissue lesions of multiple sclerosis model mouse (experimental autoimmune encephalomyelitis (EAE) mouse) induced by myelin oligodendrocyte glycoprotein (MOG), and splenocytes collected from a multiple sclerosis model mouse administered with an anti-RGM neutralizing antibody show remarkably attenuated antigen-specific and non-specific T cell activation. Furthermore, the present inventors have found that administration of an anti-RGM neutralizing antibody suppresses expression of EAE clinical symptoms in a recurrent multiple sclerosis model mouse induced by a myelin proteolipid protein (PLP); when RGMa knockdown BMDCs are stimulated with MOG and transplanted into a mouse, the expression of EAE clinical symptoms in the recipient mouse is suppressed; and when CD4+ T cell prepared from a mouse administered with an anti-RGM neutralizing antibody and MOG are stimulated with MOG and transplanted into a mouse, the expression of EAE clinical symptoms in the recipient mouse is suppressed (see Examples).

[T Cell Activation Inhibitor]

The present invention provides a T cell activation inhibitor containing an RGM inhibiting substance as an active ingredient. The RGM inhibiting substance, which is an active ingredient of the T cell activation inhibitor of the present invention, may be any of a substance that inhibits activity of RGM (RGM activity) and a substance that inhibits expression of RGM.

Examples of the substance that inhibits RGM activity include a low-molecular-weight compound, an anti-RGM neutralizing antibody and the like, which inhibit RGM activity. Examples of the index of RGM activity include an activity of RGM to bind to RGM receptor (see Example 1 (1-2)), Rap1 activation inducing activity (see Example 1 (1-3)), enhancing activity on the adhesion of T cell to ICAM (see Example 1 (1-4)) and the like. A substance that inhibits (attenuates) RGM activity when evaluated using these indices is referred to as an RGM inhibiting substance. Examples of the low-molecular-weight compound that inhibits RGM activity include Y27632 known as a Rho kinase inhibitor (M. Uehata, et al. Calcium sensitization of smooth muscle mediated by a Rho-associated protein kinase in hypertension. Nature 389, 990 (1997)).

The anti-RGM neutralizing antibody may be any as long as it is an antibody that binds to RGM and inhibits its activity, and examples thereof include an anti-RGM antibody that binds to RGM and prevents RGM from binding to RGM receptor and the like. An anti-RGM neutralizing antibody can be produced by a known method and using RGM or its fragment as an immunogen. Whether the obtained antibody is a neutralizing antibody can be confirmed using the above-mentioned index of RGM activity. Examples of RGM include, but are not limited to, human RGMa consisting of the amino acid sequence shown by SEQ ID NO: 2, rat RGMa consisting of the amino acid sequence shown by SEQ ID NO: 4 and the like. RGM derived from various organisms can be preferably used as immunogen. The amino acid sequences thereof can be easily obtained from a known database (Protein Data Bank etc.).

The anti-RGM neutralizing antibody may be a polyclonal antibody or a monoclonal antibody. It may also be a complete antibody molecule or an antibody fragment capable of specifically binding to antigen (e.g., Fab, F(ab')$_2$, Fab', Fv, scFv etc.). A polyclonal antibody can be prepared and acquired, for example, as follows. To be precise, an antigen (RGM or a fragment thereof) is dissolved in PBS, and a mammal (mouse, rat, rabbit, goat, horse etc.) is immunized with the solution optionally mixed with an appropriate amount of a conventional adjuvant (for example, complete Freund's adjuvant) as an immunogen. While the immunization method is not particularly limited, for example, a method including subcutaneous injection or intraperitoneal injection once or plural times at suitable intervals is preferable. Then, the blood is collected by a conventional method from the immunized animal, serum is separated, and a polyclonal antibody fraction is purified to give the polyclonal antibody. A monoclonal antibody can be obtained by fusing an immunocyte (for example, splenocyte) obtained from the above-mentioned immunized mammal and a myeloma cell to give hybridoma, and recovering the antibody from a culture of the hybridoma. A recombinant monoclonal antibody can also be produced by cloning an antibody gene from a hybridoma, incorporating the gene into a suitable vector, introducing the vector into a host cell, and using a gene recombination technique. Moreover, it can also be produced by a phage display method.

The anti-RGM neutralizing antibody is preferably a human chimera antibody or a humanized antibody. The human chimera antibody refers to an antibody consisting of heavy chain variable region and light chain variable region of an antibody derived from an animal other than human, and heavy chain constant region and light chain constant region of a human antibody. The humanized antibody refers to an antibody obtained by grafting CDRs (complementarity determining regions) of an antibody derived from an animal other than human to CDRs of a human antibody, and is also referred to as CDR grafted antibody, reconstitution antibody and the like. As an FR (framework region) of a humanized antibody, a region where CDR forms a good antigen binding site is selected. Where necessary, the amino acid sequence of FR in variable region of an antibody may be substituted so that CDR of the humanized antibody can form an appropriate antigen binding site. The amino acid sequence of the constant region of a human antibody can be acquired from a known database (Protein Data Bank etc.).

Examples of the substance that inhibits expression of RGM include siRNA (short interfering RNA), shRNA (short hairpin RNA), antisense oligonucleotide and the like to RGM gene. Examples of the RGM gene include, but are not limited to, a human RGMa gene consisting of the base sequence shown by SEQ ID NO: 1, a rat RGMa gene consisting of the base sequence shown by SEQ ID NO: 3 and the like. The base sequences of RGM genes derived from various organisms can be easily acquired from a known database (GenBank etc.). siRNA is a short double stranded RNA that can suppress expression of a target gene (RGM gene in the present invention). As long as being functional as siRNA, the base sequence and the length (base length) are not particularly limited. It is preferably less than about 30 bases, more preferably about 19-27 bases, more preferably about 21-25 bases. shRNA refers to a molecule having a short hairpin structure with an overhang at the 3' terminal and having about 20 base pairs or more, which is a single strand RNA partially containing a palindromic base sequence to form an intramolecularly double stranded structure. Such shRNA is, after introduced into the cell, degraded into the length of about 20 bases (typically, for example, 21 bases, 22 bases, 23 bases) in the cell, and can suppress expression of the target gene (RGM gene in the present invention) like siRNA. siRNA and shRNA may have any form as long as they can suppress expression of RGM gene. siRNA and shRNA can be chemically synthesized artificially. In addition, antisense and sense RNAs can be synthesized in vitro from template DNAs by using, for example, T7 RNA polymerase and T7 promoter. The antisense oligonucleotide only needs to be a nucleotide which is complementary to or hybridizes to continuous 5 to 100 base sequences in the DNA sequence of RGM gene, and may be any of DNA and RNA. Also, it may be modified as long as no adverse effect is imposed on the function. Antisense oligonucleotide can be synthesized by a conventional method and, for example, can be easily synthesized by a commercially available DNA synthesizer.

Thus, an RGM inhibiting substance can inhibit T cell activation by contacting with an RGM expressing cell (cell expressing RGM or cell having RGM expression activity). Therefore, the present invention encompasses a method for inhibiting T cell activation, comprising a step of contacting an RGM inhibiting substance with an RGM expressing cell.

[Pharmaceutical Composition]

The present invention provides a pharmaceutical composition for the prophylaxis or treatment of a disease caused by T cell activation, which contains the above-mentioned T cell activation inhibitor of the present invention. The pharmaceutical composition of the present invention is, in other words, a pharmaceutical composition for the prophylaxis or treatment of a disease caused by T cell activation, which contains an RGM inhibiting substance as an active ingredient.

As the disease caused by T cell activation, autoimmune diseases, cerebrovascular disorders and the like can be mentioned. Examples of the autoimmune disease include cellular autoimmune disease, rheumatism, multiple sclerosis, nervous system autoimmune disease (Guillain-Barré syndrome, neuro-Behcet's disease etc.), malignant anemia, type I (insulin-dependent) diabetes, systemic lupus erythematosus (SLE), inflammatory bowel disease (IBD), Sjogren's syndrome, atopic dermatitis, Goodpasture's syndrome, Graves' disease, autoimmune hemolytic anemia, autoimmune thrombocytopenic purpura, glomerulonephritis, myasthenia gravis, Hashimoto's disease and the like. As a cerebrovascular disorder, cerebral infarction, cerebral hemorrhage, subarachnoid hemorrhage and the like can be mentioned. Particularly, the pharmaceutical composition of the present invention is preferably used for the prophylaxis or treatment of autoimmune diseases, particularly preferably used for the prophylaxis or treatment of multiple sclerosis.

The pharmaceutical composition of the present invention can be formulated by blending an RGM inhibiting substance as an active ingredient and a pharmaceutically acceptable carrier or an additive as appropriate. Specifically it can be formulated into oral preparations such as tablet, coated tablet, pill, powder, granule, capsule, liquid, suspension, emulsion and the like; or parenteral preparations such as injection, infusion, suppository, ointment, patch and the like. The blending ratios of the carrier and additive can be appropriately set based on the ranges generally adopted in the field of pharmaceutical products. While the carrier and additive that can be blended are not particularly limited, for example, various carriers such as water, saline and other aqueous solvents, aqueous or oily base and the like; and various additives such as excipient, binder, pH adjuster, disintegrant, absorption promoter, lubricant, colorant, corrigent, flavor and the like can be mentioned.

When the RGM inhibiting substance is an anti-RGM neutralizing antibody, it is preferably administered as an injection or infusion formulated together with a pharmaceutically acceptable carrier via a parenteral administration pathway, for example, intravenously, intramuscularly, intradermally, intraperitoneally, subcutaneously or topically. An injection or infusion containing an anti-RGM neutralizing antibody can be used as a solution, a suspension or an emulsion. As the solvent therefor, for example, distilled water for injection, saline, glucose solution and isotonic solution (e.g., solutions of sodium chloride, potassium chloride, glycerol, mannitol, sorbitol, boric acid, borax, propylene glycol and the like) and the like can be used. Such injection and infusion may contain stabilizer, solubilizing agent, suspending agent, emulsifier, soothing agent, buffering agent, preservative, antiseptic, pH adjuster and the like. As the stabilizer, albumin, globulin, gelatin, mannitol, glucose, dextran, ethylene glycol, propylene glycol, ascorbic acid, sodium bisulfite, sodium thiosulfate, EDTA sodium, sodium citrate, dibutylhydroxytoluene and the like can be used. As the solubilizing agent, alcohol (e.g., ethanol etc.), polyalcohol (e.g., propylene glycol, polyethylene glycol etc.), non-ionic surfactant (e.g., polysorbate 80 (registered trade mark), HCO-50 etc.) and the like can be used. As the suspending agent, glycerol monostearate, aluminum monostearate, methylcellulose, carboxymethylcellulose, hydroxymethylcellulose, sodium lauryl sulfate and the like can be used. As the emulsifier, gum arabic, sodium alginate, tragacanth and the like can be used. As the soothing agent, benzyl alcohol, chlorobutanol, sorbitol and the like can be used. As the buffering agent, phosphate buffer, acetate buffer, borate buffer, carbonate buffer, citrate buffer, tris buffer, and the like can be used. As the preservative, methyl p-hydroxybenzoate, ethyl parahydroxybenzoate, propyl p-hydroxybenzoate, butyl p-hydroxybenzoate, chlorobutanol, benzyl alcohol, benzalkonium chloride, sodium dehydroacetate, sodium edetate, boric acid, borax and the like can be used. As the antiseptic, benzalkonium chloride, p-oxybenzoic acid, chlorobutanol and the like can be used. As the pH adjuster, hydrochloric acid, sodium hydroxide, phosphoric acid, acetic acid and the like can be used.

When the RGM inhibiting substance is a nucleic acid (siRNA, shRNA, antisense oligonucleotide and the like), it can be administered in the form of a non-viral vector or a viral vector. When it has a non-viral vector form, a method using a liposome to introduce a nucleic acid molecule (liposome method, HVJ-liposome method, cationic liposome method, lipofection method, lipophectamine method and the like), a microinjection method, a method of transferring a nucleic acid molecule into a cell together with a carrier (metal particles) by a gene gun and the like can be utilized. When siRNA or shRNA is administered to the body using a viral vector, a viral vector such as recombinant adenovirus, retrovirus and the like can be utilized. A gene can be introduced into a cell or tissue by introducing a DNA expressing siRNA or shRNA into a DNA virus or RNA virus such as detoxified retrovirus, adenovirus, adeno-associated virus, herpes virus, vaccinia virus, poxvirus, polio virus, sindbis virus, Hemagglutinating Virus of Japan, SV40 and the like to allow infection of the cell or tissue with the recombinant virus.

By administering an effective amount of the thus-obtained preparation to, for example, human and other mammals (e.g., rat, mouse, rabbit, sheep, swine, bovine, cat, dog, monkey and the like), a disease caused by T cell activation can be prevented or treated. The dose is appropriately determined in consideration of the object, severity of the disease, age, body weight, sex and past medical history of the patient, the kind of the active ingredient and the like. For example, when the active ingredient is an anti-RGM neutralizing antibody, about 0.02 mg-4000 mg per day is preferable, and about 0.1 mg-200 mg per day is more preferable, for an average human with about 65-70 kg body weight as a target. The total daily dose may be a single dose or divided doses.

[Screening Method]

The screening method of the present invention may be any as long as it comprises a step of contacting a test substance with RGM, a step of measuring the activity level of RGM contacted with the test substance, a step of comparing the measured activity level with that of RGM not contacted with the test substance, and a step of selecting a test substance that reduces the activity level of RGM. A T cell activation inhibiting substance can be conveniently and efficiently screened for by the screening method of the present invention.

A test substance can be contacted with RGM by, for example, adding the test substance to an RGM solution to allow dissolving or suspending therein. As RGM, a commercially available recombinant RGM or recombinant RGM of one's own making according to a conventional method can be used. The contact time and contact temperature are not particularly limited, and can be appropriately determined. In addition, a control group without contact with the test substance is preferably set up. The activity level of RGM can be measured based on binding activity of RGM to RGM receptor (see Example 1 (1-2)), Rap1 activation inducing activity (see Example 1 (1-3)), enhancing activity on the adhesion of T cell to ICAM (see Example 1 (1-4)) and the like as an index.

By comparison of the measured activity level with that of RGM not contacted with the test substance, whether the test substance is a T cell activation inhibiting substance can be judged. When the activity level of RGM contacted with a test substance is lower than that of RGM not contacted with the test substance, the test substance is judged to be a T cell activation inhibiting substance and is selected. Preferably, when the activity level of RGM contacted with a test substance is not more than 50%, more preferably not more than 25%, the test substance is judged to be a T cell activation inhibiting substance. A T cell activation inhibiting substance obtainable by the screening method of the present invention is useful as a candidate substance of an active ingredient of a prophylactic or therapeutic drug for a disease caused by T cell activation such as autoimmune disease and the like. Particularly, it is extremely useful as a candidate substance of an active ingredient of a prophylactic or therapeutic drug for multiple sclerosis.

EXAMPLES

The present invention is explained in detail in the following by referring to Examples, which are not to be construed as limitative.

Example 1: Expression of RGMa and RGMa Receptor in Immunocyte (1-1) Expression of RDMa in Bone Marrow-Derived Dendritic Cells (BMDCs)

According to the method of Lutz et al. (Lutz, M. B., et al. J. Immunol. Methods 223, 77-92 (1999)), bone marrow cells were collected from C57BL/6 mouse (8- to 10-week-old), and cultivated in a medium containing GM-CSF (20 ng/mL, Sigma-Aldrich) to obtain BMDCs. For the experiment, BMDCs on day 6 from the start of the culture were used.

Expression of RGMa mRNA in BMDCs was measured by real-time quantitative PCR. That is, LPS (Sigma-Aldrich) was added to BMDCs at 0, 0.01, 0.1 or 1 µg/mL on day six from the start of culture, cultured BMDCs for 24 hr and activated BMDCs were collected. Total RNA was extracted from the BMDCs by using RNeasy Kit (QUIAGEN) and cDNA was obtained by using a reverse transcriptase (GE Healthcare). Using the obtained cDNA as a template, TaqMan real-time PCR (ABI Prism 7500 Sequence Detection System) was performed according to the manufacturer's protocol, and mRNA expression of RGMa was quantitatively analyzed. Specific primers and probes were purchased from Applied Biosystems.

In addition, expression of RGMa in BMDCs was detected by Western blotting. That is, BMDCs ($2\times10^6$ cells) at 24 hr from the LPS addition were dissolved in 2× sample buffer (250 mM Tris-HCl, 4% SDS, 20% glycerol, 0.02% bromophenol blue and 10% β-mercaptoethanol), boiled for 5 min, and an equal amount of each sample was subjected to 15% SDS-PAGE under reducing conditions. After electrophoresis, the protein was transferred onto PVDF membrane (Immobilon-P, Millipore). After blocking with PBS containing 5% skim milk and 0.05% Tween 20, the protein was reacted with an anti-RGMa antibody (antibody produced by the present inventors, see non-patent document 3), and detected using an ECL chemical luminescence system (GE Healthcare) and an HRP-labeled secondary antibody (Cell Signaling Technology). Protein band was quantified using Scion image.

Figure 2:
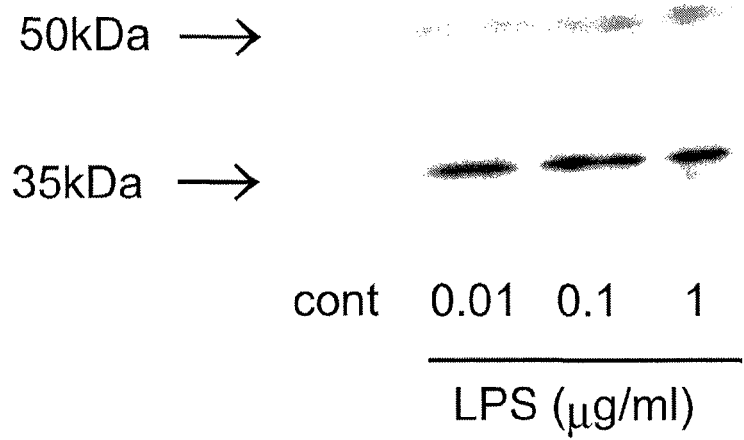
FIG. 2 shows the results of detecting the expression of RGMa in BMDCs stimulated with LPS, by Western blotting.

The results of the real-time PCR are shown in FIG. 1, and the results of Western blotting are shown in FIG. 2. As is clear from FIG. 1, the expression of RGMa mRNA in BMDCs was enhanced by the stimulation with LPS. In addition, as is clear from FIG. 2, 35 kDa and 50 kDa bands showing the binding of the anti-RGMa antibody existed, and an amount in the cell increased by LPS stimulation. The 50 kDa band corresponds to the full length of RGMa, and the 35 kDa band is a C-terminal fragment of RGMa and is assumed to be a mature form of RGMa (Mueller, B. K., Yamashita, T., Schaffar, G. & Mueller, R. Philos. Trans. R. Soc. Lond. B Biol. Sci. 361, 1513-1529 (2006)). These results have clarified that the expression of RGMa is induced in activated BMDCs.

(1-2) Expression of RGMa Receptor in $CD4^+$ T Cell and $CD11b^+$ Macrophage

The spleen was isolated from C57BL/6 mouse (8- to 10-week-old), rapidly placed in a RPMI1640 medium (Invitrogen), gently pressed, and a treatment for removing red blood cells was performed with an ACK lysis buffer (Lonza Walkersville) to give a cell suspension. After washing three times with RPMI1640, the cell suspension was filtered through a 70 µm cell strainer to give a splenocyte single cell suspension. To this suspension were added various concentrations of human RGMa C-terminal fragment (hereinafter to be referred to as "RGMa-Fc") and the suspension was incubated for 30 min. After washing, immunostaining using PE-labeled anti-CD11b antibody or APC-labeled anti-CD4 antibody, and FITC-labeled anti-human RGMa-Fc antibody (BD Biosciences) in combination was performed, and the binding of the cells and human RGMa-Fc was measured by flow cytometry analysis. For flow cytometry analysis, FACSCalibur (BD Biosciences) and CellQuest software (BD Biosciences) were used.

Figure 3:
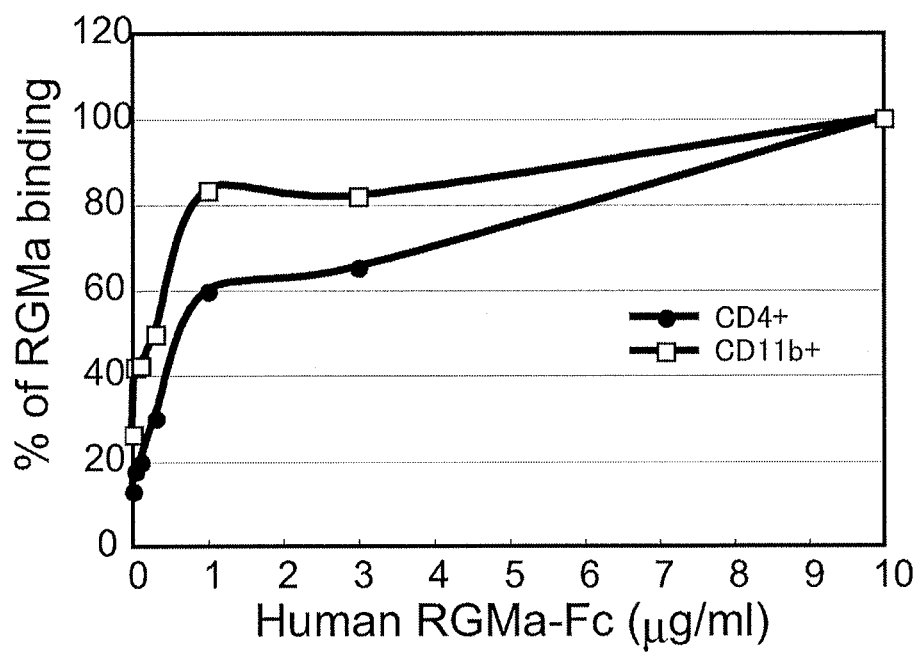
FIG. 3 shows the results of the flow cytometry analysis of the binding of CD4$^+$ T cells or CD11b$^+$ macrophages, and various concentrations of human RGMa-Fc.

The results are shown in FIG. 3. As is clear from FIG. 3, both the spleen-derived $CD4^+$ T cell and $CD11b^+$ macrophage bound to human RGMa-Fc in a concentration dependent manner. The result has clarified that these cells express an RGMa receptor.

(1-3) Study of Rap1 Activation in $CD4^+$ T Cell and $CD11b^+$ Macrophage

Signal transduction possibly mediated by RGMa bound to $CD4^+$ T cell and $CD11b^+$ macrophage was investigated. It is known that, in T lymphocytes, TCR ligation induces temporary activation of Rap1 and accumulation of Rap1-GTP in a contacting surface of T cell to antigen presenting cell, which regulates the signal mediated by LFA-1 (integrin): ICAM-1 (integrin ligand) (Katagiri, K. et al. Mol. Cell Biol. 20, 1956-1969 (2000), Katagiri, K., Hattori, M., Minato, N. & Kinashi, T. Mol. Cell Biol 22, 1001-1015 (2002)). Thus, the involvement of RGMa in Rap1 activation in $CD4^+$ T cell and $CD11b^+$ macrophage was evaluated.

$CD4^+$ T cells and $CD11b^+$ macrophages were isolated by positive sorting respectively using anti-CD4 magnetic beads and anti-CD11b magnetic beads (Miltenyi Biotec) from the splenocyte single cell suspension prepared in the above-mentioned (1-2), and active form Rap1 was measured. For the measurement of active form Rap1, Rap1 activation assay kit (Upstate Biotech) was used, and splenocytes before isolation of CD4$^+$ T cells and CD11b$^+$ macrophages were used as a control. To be specific, 2 μg/mL recombinant mouse RGMa (R&D Systems) was added to each cell suspension, the mixture was treated for 5 min, and lysed in Mg$^{2+}$ lysis buffer (containing 25 mM HEPES (pH 7.5), 150 mM NaCl, 1% Igepal CA-630, 10 mM MgCl$_2$, 1 mM EDTA, 2% glycerol, 2 mM sodium orthovanadate, 1 mM ethylsulfonyl fluoride, and protease inhibitor cocktails (Roche Diagnostics)). The cell lysate was used for the measurement of total Rap1. RalGDS-bound agarose and the cell lysate were reacted at 4° C. for 30 min to precipitate active form Rap1 bound to a Ral-binding domain. The beads were washed with Mg$^{2+}$ lysis buffer, resuspended in 2× sample buffer and subjected to Western blotting. For Western blotting, anti-Rap1 antibody attached to the kit was used, and the procedures similar to those in the above-mentioned (1-1) were followed. Band was quantified using Scion image and relative Rap1 activation level was calculated.

Figure 4A:
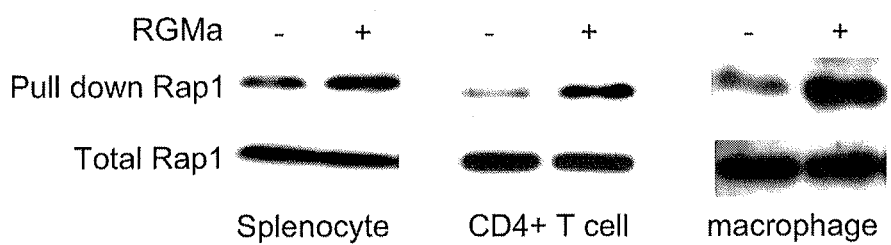
FIG. 4(A) shows the results of detecting total Rap1 and active form Rap1 in CD4$^+$ T cells and CD11b$^+$ macrophage by Western blotting.
Figure 4B:
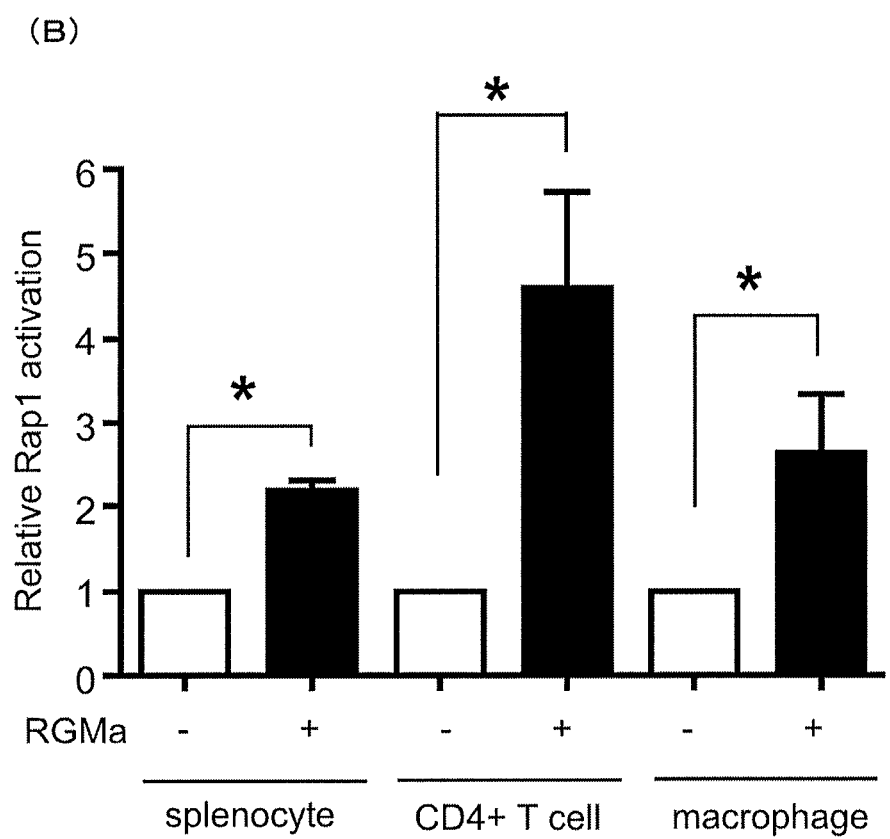
FIG. 4(B) shows the relative Rap1 activation levels calculated from quantification of the bands in Western blotting of FIG. 4(A) by using Scion image.

The results of Western blotting are shown in FIG. 4(A), and a graph showing relative Rap1 activity is shown in FIG. 4(B). In FIG. 4(B), the graph of relative activity values is shown in mean and standard error of 3 or 4 independent experiments, and "*" means P<0.05 in Student t-test. As is clear from FIG. 4(A), active form Rap1 (Pull down Rap1 in the Figure) increased by the treatment with mouse RGMa in all cells. As shown in FIG. 4(B), it has been clarified that RGMa stimulation for 5 min significantly activates Rap1 in splenocyte, CD4$^+$ T cell and CD11b$^+$ macrophage. These results suggest the possibility of RGMa expressed in dendritic cell activating intracellular Rap1 via RGMa receptor on the surface of CD4$^+$ T cell and CD11b$^+$ macrophage.

(1-4) Lymphocyte Binding Assay

Adhesion mediated by integrin plays a central role in trafficking and activation of T cell. Furthermore, adhesion induced by TCR requires activation of Rap1 (Katagiri, K. et al. Mol. Cell Biol. 20, 1956-1969 (2000), Reedquist, K. A. et al. J. Cell Biol. 148, 1151-1158 (2000), Suga, K. et al. FEBS Lett. 489, 249-253 (2001)). To confirm whether or not active form Rap1 induced by RGMa involves in the adhesion activity, a lymphocyte binding assay was performed.

Cell adhesion was evaluated according to the method described in prior art references (Sebzda, E., Bracke, M., Tugal, T., Hogg, N. & Cantrell, D. A. Nat. Immunol. 3, 251-258 (2002), Duchniewicz, M. et al. Mol. Cell Biol. 26, 643-653 (2006)). That is, 2 μg/mL recombinant mouse ICAM-1/Fc (R&D Systems) or 4 μg/mL fibronectin (Sigma-Aldrich) was added to a 96-well flat plate (NUNC, Max-iSorp), and left standing at 4° C. overnight for pre-coating. The plate was washed with PBS, and blocked with RPMI1640 (Invitrogen) containing 2% BSA at 37° C. for 1 hr to prevent non-specific binding. The plate coated with ICAM-1/Fc was used for the evaluation of CD4$^+$ T cell, and the plate coated with fibronectin was used for the evaluation of splenocyte.

Freshly prepared splenocytes or CD4$^+$ T cells were labeled with 2.5 μM BCECF-AM (2'7'-bis-(2-carboxyethyl)-5-(and -6)-carboxyfluorescein, acetoxymethyl ester, Calbiochem) at 37° C. for 30 min, and then washed with RPMI1640 containing 0.5% BSA. 5×10$^5$ cells were added to the pre-coated plate, and incubated in 0.5% BSA-containing RPMI1640 containing or not containing 2 μg/mL recombinant RGMa at 37° C. for 1 hr. The cells that did not adhere were removed by washing three times with warm 0.5% BSA-containing RPMI1640. The adhesion was quantified using Spectra MAX (Molecular Devices) at an excitation wavelength of 485 nm and a fluorescence wavelength of 538 nm. The adhesion ratio was shown in percentage to the total number of cells seeded in one well.

Figure 5B:
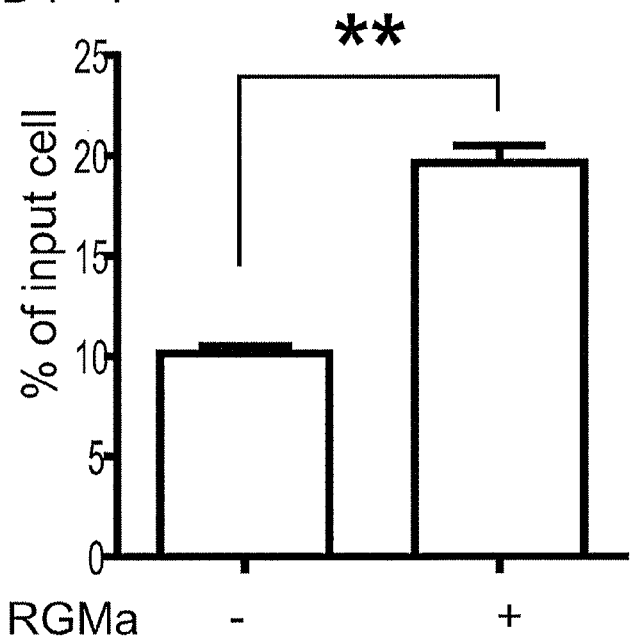
FIG. 5(B) shows the results of measuring adhesion ratio of CD4$^+$ T cell to ICAM1 in the presence or absence of stimulation with RGMa.

The results for splenocyte are shown in FIG. 5(A), and the results for CD4$^+$ T cell are shown in FIG. 5(B). The graph of the adhesion ratio shows mean and standard error of three independent experiments, and "*" and "" show P<0.05 and P<0.01, respectively, in Student's t-test. As is clear from FIG. 5(A), splenocytes stimulated with RGMa show significantly higher ratio of adhesion to fibronectin as compared to splenocytes free of RGMa stimulation. Similarly, as is clear from FIG. 5**(B), CD4$^+$ T cells stimulated with RGMa show significantly higher ratio of adhesion to ICAM-1 as compared to CD4$^+$ T cells free of RGMa stimulation. These results have clarified that activation of Rap1 by RGMa enhances the adhesion activity of splenocyte and CD4$^+$ T cell.

Example 2: Study of Effect of Anti-RGMa Neutralizing Antibody in Multiple Sclerosis Model Mouse (2-1) Production of Multiple Sclerosis Model Mouse As an animal model widely accepted as an experiment model of clinical and pathological characteristics of multiple sclerosis, an experimental autoimmune encephalomyelitis (hereinafter to be referred to as "EAE") mouse induced with myelin oligodendrocyte glycoprotein (hereinafter to be referred to as "MOG") was used. Specifically, EAE was induced by subcutaneously administering an emulsion (200 μL) of 100 μL of PBS containing (MOG)$_{35-55}$ peptide (MEVGWYRSPFSRVVHLYRNGK (SEQ ID NO: 5), Greiner Bio-one, 100 μg) and 100 μL of complete Freund's adjuvant containing killed tuberculosis (H37Ra, Difco, 500 μg) to the side of C57BL/6 mouse (8- to 10-week-old). Furthermore, 200 ng of pertussis toxin (List Biological Laboratories) was intravenously administered after MOG administration and 48 hr thereafter.

(2-2) Observation of Clinical Symptom Caused by Administration of Anti-RGMa Neutralizing Antibody to Multiple Sclerosis Model Mouse On Days 7 and 10 after MOG administration, an anti-RGMa neutralizing antibody produced by the present inventors (see non-patent document 3) or a control antibody (rabbit IgG, Sigma-Aldrich) (each 400 μg) was intraperitoneally administered. The anti-RGMa neutralizing antibody administration group consisted of 9 EAE mice, and the control antibody administration group consisted of 11 EAE mice. The groups were observed from MOG administration (Day 0) to Day 21, and clinical symptoms of EAE were evaluated based on the following criteria.

0: no abnormality
0.5: loss of tail tension
1: loss of tail reflection
2: loss of tail reflection, decreasing of righting reflex, abnormal perception of one limb
3: abnormal perception and paralysis of one limb
3.5: paralysis of both hindpaws
4: paralysis of forepaw and hindpaw
5: dying, dead After completion of the observation, the mouse was euthanized, the spinal cord was isolated, fixed with paraformaldehyde, and paraffin embedded slices were produced and subjected to a histological evaluation. The pieces were stained with hematoxylin-eosin (HE), and inflammation was evaluated. From the cervical spinal cord to the thoracic spinal cord, 20-30 slices were observed per mouse, and semi-quantitative inflammation was histologically evaluated (inflammation index) in blind based on the following criteria. Five mice from the anti-RGMa neutralizing antibody administration group were evaluated, and 6 mice from the control antibody administration group were evaluated.

Figure 6:
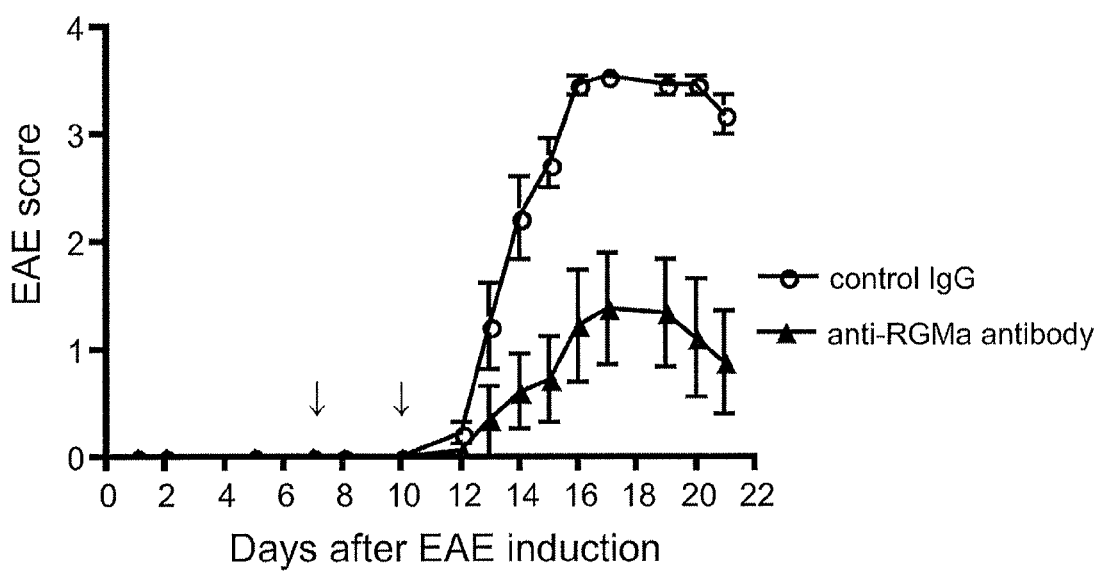
FIG. 6 shows the observation results of time-course changes in the quantified scores of the clinical symptoms of experimental autoimmune encephalomyelitis (EAE) in multiple sclerosis model mouse administered with an anti-RGMa neutralizing antibody and multiple sclerosis model mouse administered with a control antibody.

0: no inflammation
1: cell infiltration only around blood vessels and meninges
2: mild cell infiltration of bone marrow parenchyma
3: moderate cell infiltration of bone marrow parenchyma
4: severe cell infiltration of bone marrow parenchyma Changes in EAE score during the observation period are shown in FIG. 6. The EAE score are shown in mean and standard error. As is clear from FIG. 6, the EAE scores of the anti-RGMa neutralizing antibody administration group were remarkably low as compared to those of the control antibody administration group from day 14. Although not shown in the Figure, the results of Student's t-test reveal a statistically significant differences of P<0.05 on Day 14 and P<0.01 from day 15 between the both groups.

Figure 7:
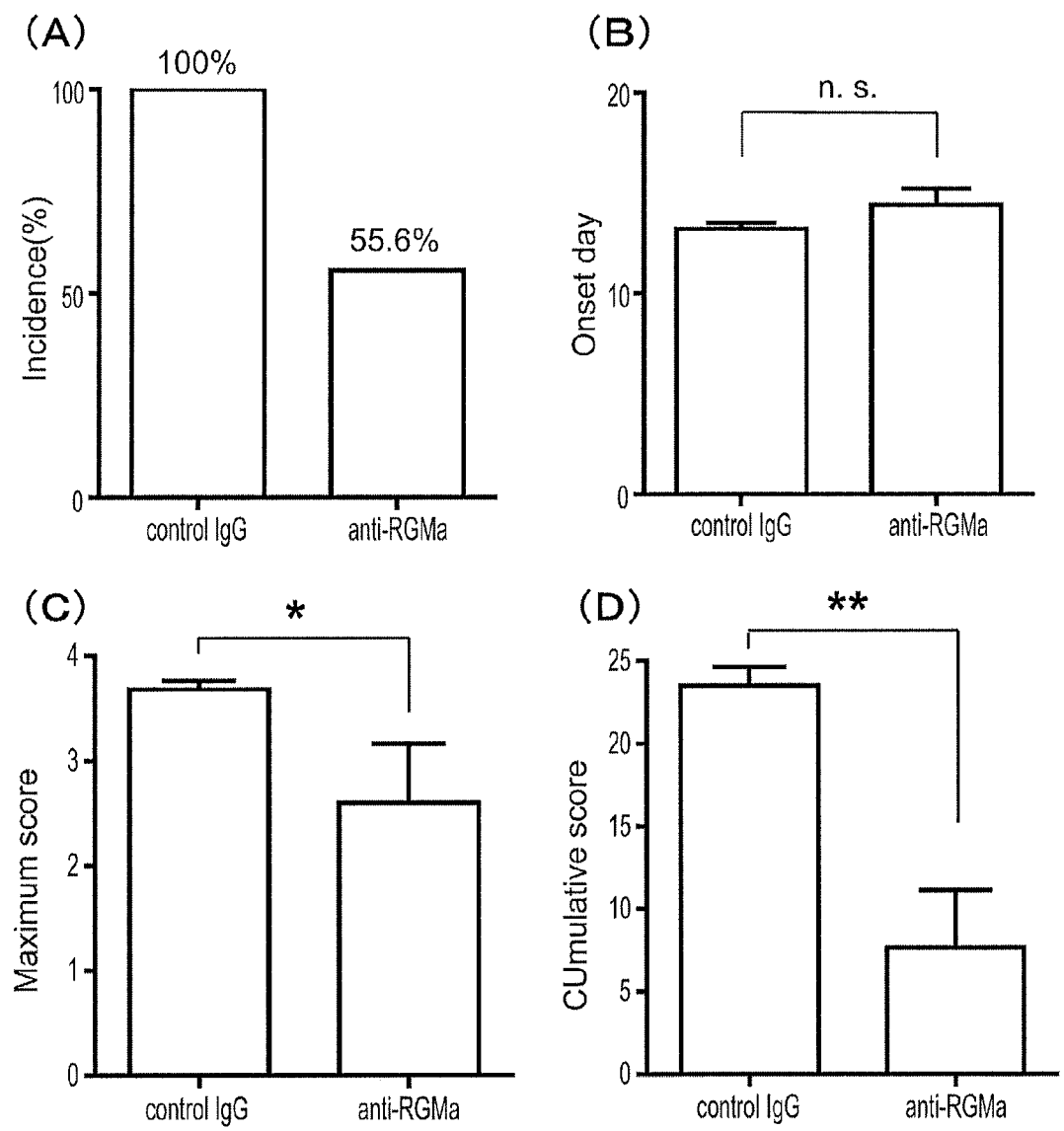
FIG. 7(A) shows expression ratio of clinical symptom of EAE in each group, (B) shows average of EAE onset days in each group, (C) shows average of maximum EAE score of each mouse in each group, and (D) shows average of cumulative EAE score of each mouse in each group.

The EAE clinical symptom expression ratio of each group is shown in FIG. 7(A), average EAE onset date of each group is shown in FIG. 7(B), average maximum value of the score of each mouse in each group is shown in FIG. 7(C), and average cumulative score of each mouse in each group is shown in FIG. 7(D). In the Figures, "n.s." means no significant difference in Student's t-test, and "*" and "**" mean P<0.05 and P<0.01, respectively, in Student's t-test. As is clear from FIG. 7(A), while all cases (100%) of the control antibody administration group expressed the clinical symptom of EAE, 44% of mice of the anti-RGMa neutralizing antibody administration group did not express clinical symptom of EAE. As is clear from FIG. 7(B), the onset dates of the both groups were not different, which shows administration of anti-RGMa neutralizing antibody does not delay the onset of EAE. On the other hand, as is clear from FIG. 7(C) and (D), both the average maximum score and the average cumulative score were significantly lower in the anti-RGMa neutralizing antibody administration group than in the control antibody administration group. These results show that the administration of anti-RGMa neutralizing antibody is effective for the suppression of the expression of EAE symptoms and the suppression of the progression thereof.

Figure 8:
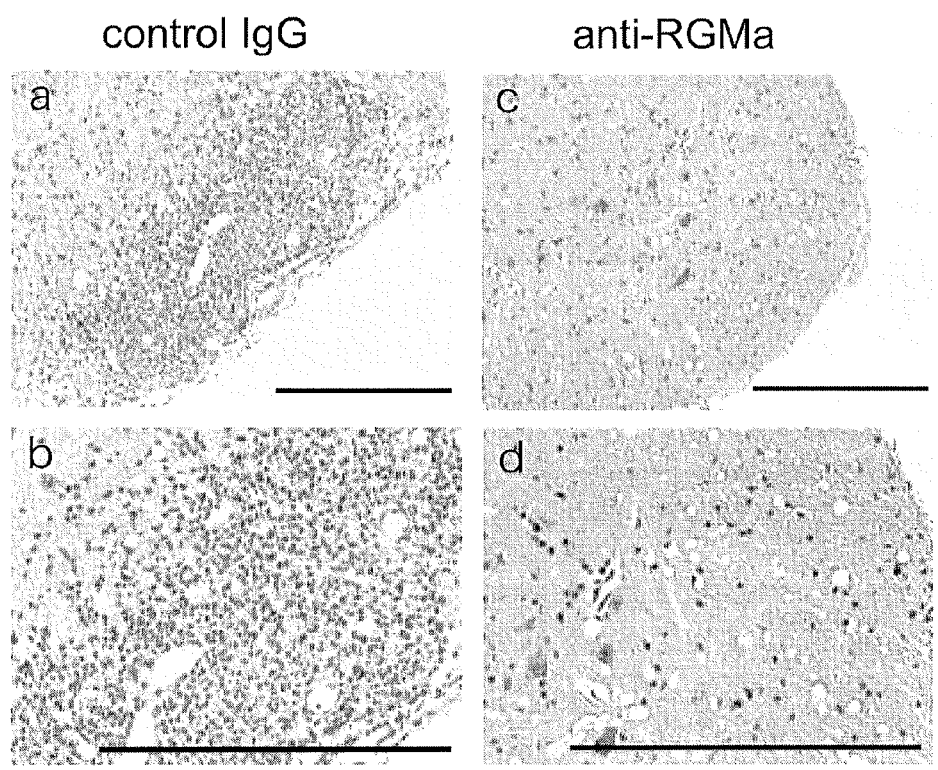
FIGS. 8(a) and (b) show HE-stained histology of the cervical spinal cord of multiple sclerosis model mouse administered with control antibody, and (c) and (d) show HE-stained histology of the cervical spinal cord of multiple sclerosis model mouse administered with anti-RGMa neutralizing antibody.

The HE-stained histology of the cervical spinal cord is shown in FIG. 8, wherein (a) and (b) are HE-stained histology of the control antibody administration group, (c) and (d) are HE-stained histology of the anti-RGMa neutralizing antibody administration group, and the scale bar shows 250 µm. As is clear from FIGS. 8(a) and (b), inflammatory mononuclear cells are widely present and inflammatory lesions are widespread in the bone marrow of the control antibody administration group. On the other hand, as is clear from (c) and (d), the number of inflammatory mononuclear cells is remarkably small in the bone marrow of the anti-RGMa neutralizing antibody administration group, which indicates that inflammation lesion has been reduced.

Figure 9:
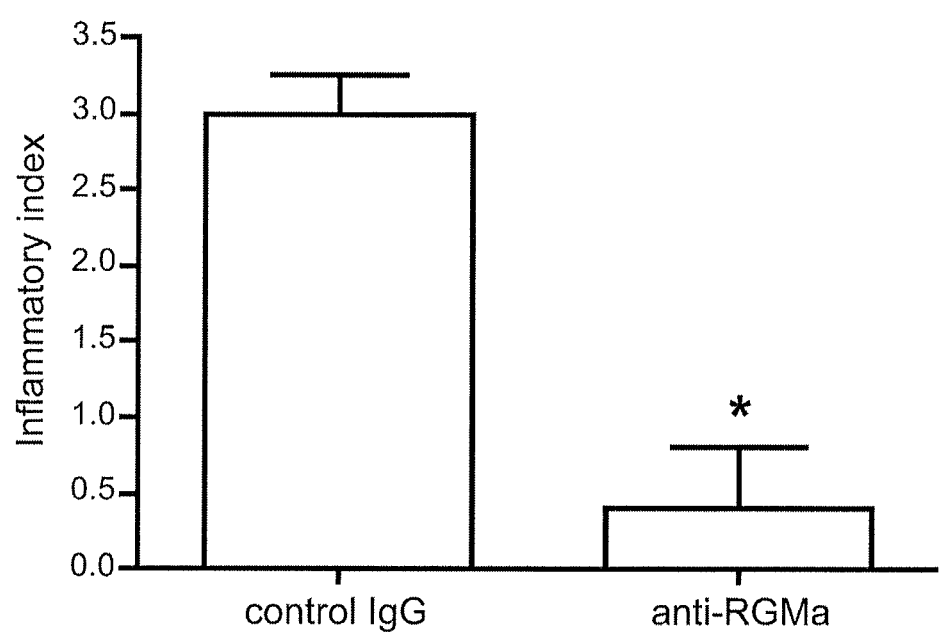
FIG. 9 shows the results of inflammation levels, quantified based on an inflammatory index, of a bone marrow tissue sample of multiple sclerosis model mouse administered with control antibody and a bone marrow tissue sample of multiple sclerosis model mouse administered with anti-RGMa neutralizing antibody.

The evaluation results of the inflammatory index are shown in FIG. 9, wherein "*" shows P<0.05 in Student's t-test. As is clear from FIG. 9, the inflammation index of the anti-RGMa neutralizing antibody administration group showed a significantly low value as compared to the control antibody administration group. As shown above, the experiment results using multiple sclerosis model mice have clarified that administration of anti-RGMa neutralizing antibody reduces both the clinical symptoms and histological lesion in EAE.

Example 3: Study of T Cell Activation in Splenocyte of Multiple Sclerosis Model Mouse Administered with Anti-RGMa Neutralizing Antibody On Day 21 after MOG administration, the spleen was isolated from the multiple sclerosis model mouse (EAE mouse) of Example 2 after completion of the clinical symptom observation. Splenocytes were isolated, seeded in a 96-well plate at $5 \times 10^5$ cells/well, cultured for 3 days to analyze cell proliferation. As the medium, RPMI1640 medium containing glutamine, sodium pyruvate, penicillin, streptomycin, 2-ME and 10% heat-inactivated FBS was used. For re-stimulation of CD4$^+$ T cell, 20 µg/mL MOG peptide or 5 µg/mL anti-CD3 monoclonal antibody (2C11, BD Biosciences) was added when cultivation was started. According to the method of Kubo et al. (Kubo, T., et al. J. Immunol. 173, 7249-7258 (2004)), [$^3$H]thymidine uptake for 18 hr before completion of the cultivation was evaluated.

For measurement of the production amounts of IFN-γ, IL-2, IL-4 and IL-17, the above-mentioned splenocytes were seeded in a 24-well plate at $2 \times 10^6$ cells/well, and cultured in the presence or absence of 20 µg/mL MOG peptide or 5 µg/mL anti-CD3 monoclonal antibody. The culture supernatant at 24 hr from the start of the cultivation was used for IL-2 measurement, and the culture supernatant at 72 hr from the start of the cultivation was used for the measurement of other cytokines. The cytokine measurement was performed using ELISA kit (Invitrogen) and according to the instructions thereof.

Figure 10:
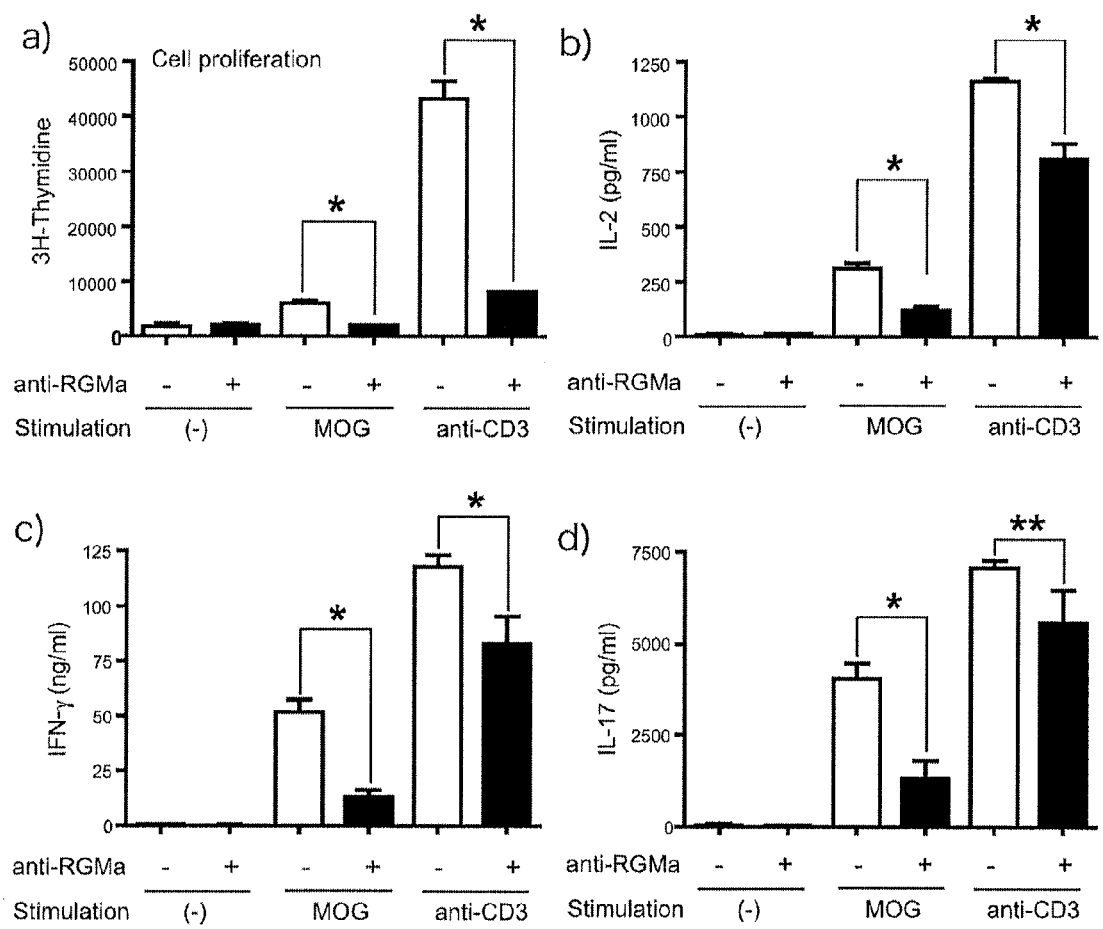
FIG. 10 shows the results of examining antigen-specific T cell activation and non-specific T cell activation of splenocytes prepared from multiple sclerosis model mouse administered with control antibody and multiple sclerosis model mouse administered with anti-RGMa neutralizing antibody, wherein (a) shows cell proliferation, (b) shows IL-2 secretion amount, (c) shows IFN-γ secretion amount, and (d) shows IL-17 secretion amount.

The results are shown in FIG. 10, wherein (a) shows the measurement results of cell proliferation, (b) shows the measurement results of IL-2, (c) shows the measurement results of IFN-γ, and (d) shows the measurement results of IL-17. Each graph shows mean and standard error (n=6 in control antibody administration group, n=5 in anti-RGMa neutralizing antibody administration group), and "*" and "**" show P<0.05 and P<0.01, respectively, in Student's t-test. As is clear from FIG. 10(a), the cell proliferation of splenocytes obtained from the mouse of the anti-RGMa neutralizing antibody administration group was significantly lower than that of splenocytes obtained from the mouse of the control antibody administration group, both in the cases of antigen-specific stimulation by MOG peptide and non-specific stimulation by anti-CD3 monoclonal antibody. In addition, as is clear from FIGS. 10(b), (c) and (d), the amounts of IL-2, IFN-γ and IL-17 secreted from the splenocytes obtained from the mouse of the anti-RGMa neutralizing antibody administration group was significantly lower than those from the splenocytes obtained from the mouse of the control antibody administration group, both in the cases of antigen-specific stimulation by MOG peptide and non-specific stimulation by anti-CD3 monoclonal antibody. Although the data are not shown, the secretion amount of IL-4 was not influenced by the administration of anti-RGMa neutralizing antibody. These results have clarified that the administration of anti-RGMa neutralizing antibody to EAE mouse remarkably attenuates antigen-specific and non-specific T cell activations in EAE mouse.

Example 4: Study of Effect of Anti-RGMa Neutralizing Antibody in Recurrent Multiple Sclerosis Model Mouse (4-1) Preparation of Recurrent Multiple Sclerosis Model Mouse Instead of MOG, myelin proteolipid protein (hereinafter to be referred to as "PLP") was administered to SJL/J mouse to prepare a recurrent EAE model mouse. Specifically, recurrent EAE was induced by subcutaneously administering an emulsion (200 μL) of 100 μL of PBS containing (PLP)$_{139-151}$ peptide (HSLGKWLGHPDKF (SEQ ID NO: 6), Greiner Bio-one, 100 μg) and 100 μL of complete Freund's adjuvant containing killed tuberculosis (H37Ra, Difco, 500 μg) to the side of SJL/J mouse (8- to 10-week-old). Furthermore, 200 ng of pertussis toxin (List Biological Laboratories) was intravenously administered after PLP administration and 48 hr thereafter.

(4-2) Observation of Clinical Symptoms by Administration of Anti-RGMa Neutralizing Antibody to Recurrent Multiple Sclerosis Model Mouse An anti-RGMa neutralizing antibody produced by the present inventors (see non-patent document 3) or a control antibody (rabbit IgG, Sigma-Aldrich) was intraperitoneally administered by 400 μg each on days 25 and 28 after PLP administration. The anti-RGMa neutralizing antibody administration group consisted of 9 EAE mice, and the control antibody administration group consisted of 11 EAE mice. The clinical symptoms of EAE were observe from PLP administration (day 0) to day 45, and evaluated based on the criteria described in the above-mentioned Example 2.

Figure 11:
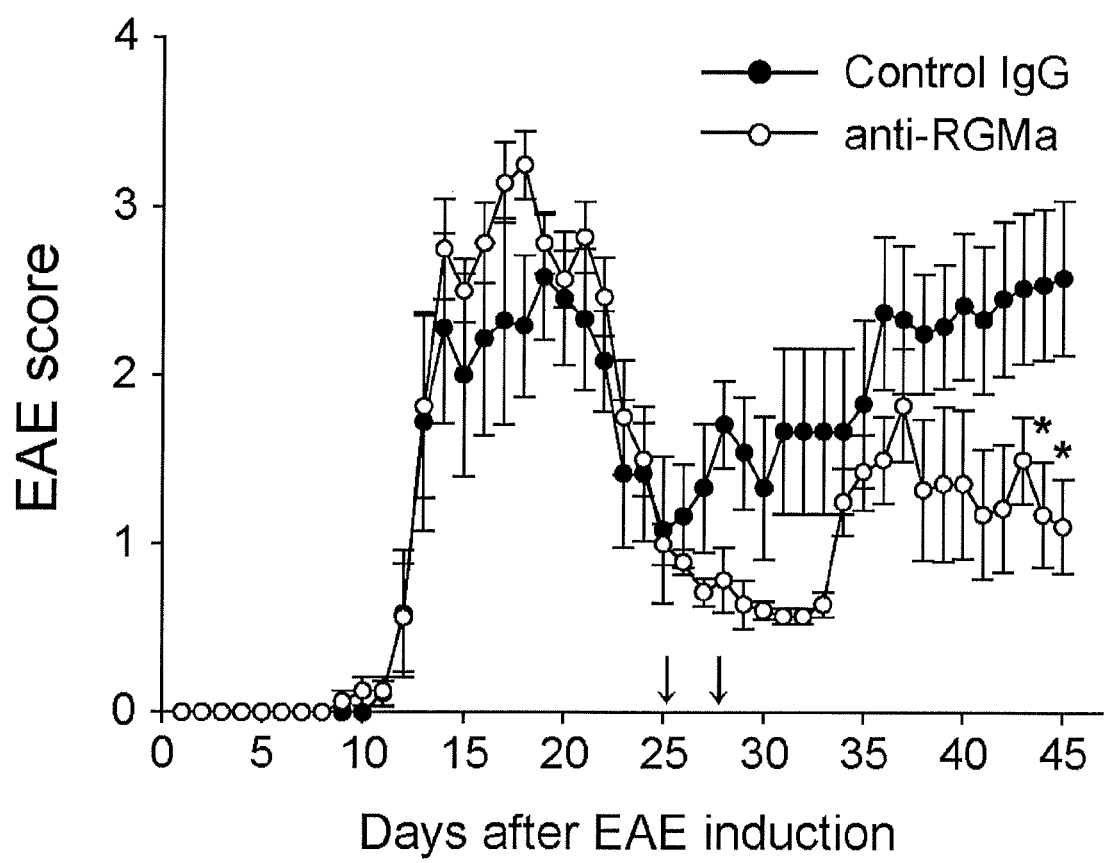
FIG. 11 shows the observation results of time-course changes in the quantified scores of the clinical symptoms of EAE in recurrent multiple sclerosis model mouse administered with an anti-RGMa neutralizing antibody and multiple sclerosis model mouse administered with a control antibody.

Changes in the EAE score during the observation period are shown in FIG. 11. The EAE score are shown in mean and standard error, wherein "*" shows P<0.05 in Student's t-test. As is clear from FIG. 11, EAE score of the anti-RGMa neutralizing antibody administration group after antibody administration was remarkably lower than that of the control antibody administration group. These results have revealed that administration of anti-RGMa neutralizing antibody in the latter stage of the first paralysis expression stage can prevent recurrence of EAE.

Example 5: Study of Effect of RGMa Gene Knockdown on Clinical Symptom of EAE in Mouse Transplanted with BMDCs Stimulated by MOG (5-1) Preparation of RGMa Gene Knockdown BMDCs Mouse RGMa siRNA (Stealth RNAi (trade name), Invitrogen) having the base sequences shown below was purchased and used. In addition, non-targeting dsRNA (Invitrogen) was used as control siRNA.

```
sense strand:
                                (SEQ ID NO: 7)
5'-AAAGAGGCCGCAGUGAGUGUAGUUG-3' antisense strand:
                                (SEQ ID NO: 8)
5'-CAACUACACUCACUGCGGCCUCUUU-3'
```

BMDCs on day 7 after the start of culture were used (see Example 1). 1×10$^6$ BMDCs were suspended in 100 μL of a solution for nucleic acid introduction containing 500 pmol of mouse RGMa siRNA or control siRNA. The sample was transferred to a cuvette, and siRNA was introduced into the cells using Nucleofector (registered trade mark) (Lonza) and according to the manufacturer's handling explanation. After siRNA introduction, the cells were cultivated in RPMI1640 medium added with glutamine, sodium pyruvate, penicillin, streptomycin, 2-ME and 10% heat-inactivated FBS. The expression of RGMa in BMDCs introduced with mouse RGMa siRNA remarkably decreased.

(5-2) MOG Stimulation and Transplantation to Mouse

BMDCs introduced with mouse RGMa siRNA or control siRNA were added with 100 μg/mL (MOG)$_{35-55}$ peptide, and cultured for 4-6 hr to allow antigen stimulation. The viable cells (6×10$^5$) after stimulation were intravenously administered to a recipient mouse (C57BL/6). Then, complete Freund's adjuvant (200 μL) containing killed tuberculosis (H37Ra, Difco, 500 μg) was subcutaneously administered. 48 hr thereafter, 200 ng of pertussis toxin (List Biological Laboratories) was intravenously administered.

(5-3) Observation of EAE Clinical Symptom

RGMa siRNA group (5 mice) and control siRNA group (5 mice) were observed from cell transplantation (day 0) to day 21, and clinical symptoms of EAE were evaluated based on the criteria described in Example 2 above.

Figure 12:
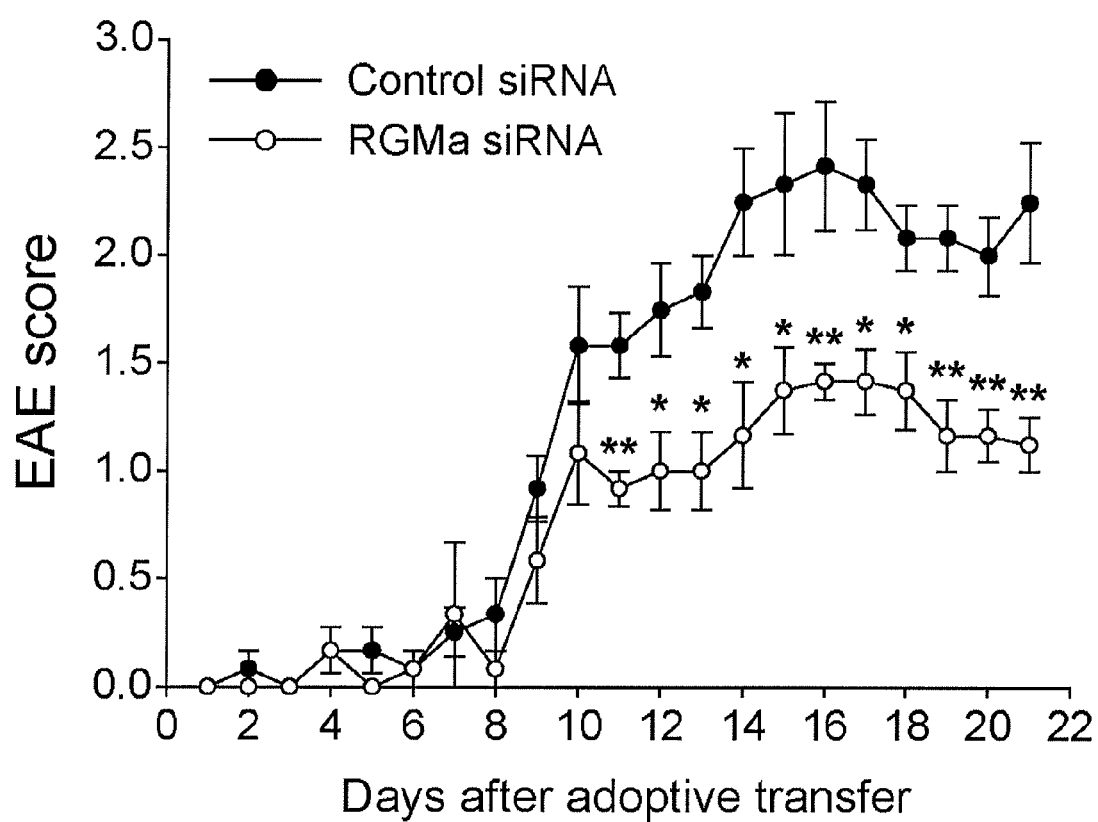
FIG. 12 shows the observation results of time-course changes in the quantified scores of the clinical symptoms of EAE in recipient mouse transplanted with BMDCs with RGMa gene knockdown or BMDCs without RGMa gene knockdown, each after stimulation with MOG.

Changes in the EAE score during the observation period are shown in FIG. 12. The EAE score are shown in mean and standard error, wherein "*" and "**" show P<0.05 and P<0.01, respectively, in Student's t-test. As is clear from FIG. 12, EAE score of the RGMa siRNA group was remarkably lower than that of the control siRNA group. The results have clarified the effectiveness of RGMa siRNA for the prophylaxis or treatment of multiple sclerosis.

Example 6: Study of Effect of Anti-RGMa Neutralizing Antibody on Clinical Symptom of EAE in Mouse Transplanted with CD4$^+$ T Cell Stimulated with MOG (6-1) Preparation of Donor Mouse CD4$^+$ T Cells An anti-RGMa neutralizing antibody produced by the present inventors (see non-patent document 3) or a control antibody (rabbit IgG, Sigma-Aldrich) was intraperitoneally administered by 400 μg to a donor mouse (C57BL/6) (day −2). Two days later (day 0), the anti-RGMa neutralizing antibody or control antibody was administered for the second time, and an emulsion (200 μL) of 100 μL of PBS containing (MOG)$_{35-55}$ peptide (100 μg) and 100 μL of complete Freund's adjuvant containing killed tuberculosis (H37Ra, Difco, 500 μg) was subcutaneously administered. Five days later (day 5), the anti-RGMa neutralizing antibody or control antibody was administered for the third time. On the 10th day from the MOG administration, the mouse was euthanized, and the spleen and the draining lymph node were isolated. The cells were isolated and a cell suspension was prepared. For re-stimulation of CD4$^+$ T cells, the cells (1×10$^6$ cells/mL) were cultured for 3 days in a medium containing 40 μg/mL (MOG)$_{35-55}$ peptide. After completion of the cultivation, the cells were collected and CD4$^+$ T cells were separated using a CD4$^+$ T cell separation kit (Miltenyi Biotec).

(6-2) Transplantation to Recipient Mouse and Observation of EAE Clinical Symptoms A sublethal amount of radiation (500 Gy) was irradiated in advance to the recipient mouse (C57BL/6). CD4$^+$ T cells (viable cells, 6×10$^5$) were intravenously administered to the recipient mouse. The mice transplanted with CD4$^+$ T cells derived from a donor mouse administered with an anti-RGMa neutralizing antibody (anti-RGMa neutralizing antibody group, 7 mice) and the mice transplanted with CD4$^+$ T cells derived from a donor mouse administered with a control antibody (control antibody group, 7 mice) were observed from cell transplantation (day 0) to day 21, and clinical symptoms of EAE were evaluated based on the criteria described in Example 2 above.

Figure 13:
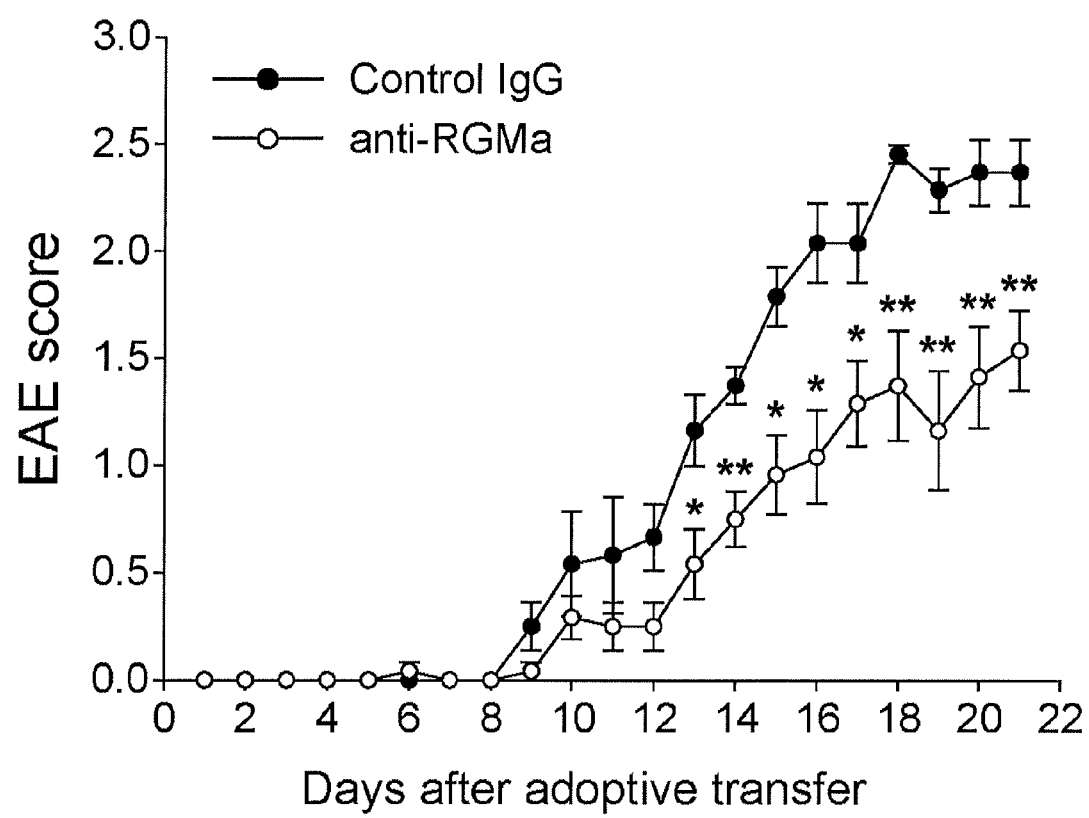
FIG. 13 shows the observation results of time-course changes in the quantified scores of the clinical symptoms of EAE in recipient mouse transplanted with CD4$^+$ T cells, which were prepared from donor mouse administered with anti-RGMa neutralizing antibody or control antibody, and MOG, and subjected to MOG stimulation.

Changes in the EAE score during the observation period are shown in FIG. 13. The EAE score are shown in mean and standard error, wherein "*" and "**" show P<0.05 and P<0.01, respectively, in Student's t-test. As is clear from FIG. 13, EAE score of the anti-RGMa neutralizing antibody group was remarkably lower than that of the control antibody group. The results have clarified that the prophylactic or therapeutic effect of an anti-RGMa neutralizing antibody for multiple sclerosis is based on suppression of antigen-specific T cell activation and differentiation of self-reactive T cell by anti-RGMa neutralizing antibody.

The foregoing results have clarified that RGMa is involved in the onset of EAE caused by enhanced immune responses such as infiltration of mononuclear cells into the spinal cord and activation of T cells, for example, proliferation of T cells, and production of EAE-related cytokines IL-2, IL-17 and IFN-γ. Moreover, they show that an anti-RGMa neutralizing antibody and RGMa siRNA inhibit activation of T cell and are effective for the prophylaxis or treatment of multiple sclerosis.

The present invention is not limited to the aforementioned respective embodiments and Examples, and can be modified in various manners within the scope defined by the claims. Thus, embodiments obtained by appropriately combining the technical means respectively disclosed in different embodiments are also encompassed in the technical scope of the present invention. In addition, all academic documents and patent documents described in the present specification are quoted for reference in the present specification.

INDUSTRIAL APPLICABILITY

The present invention has an extremely high utility value in the pharmaceutical product industry.

The invention claimed is:

1. An in vivo method of inhibiting activation of a T cell by a Repulsive Guidance Molecule (RGM) expressing cell, comprising
   a step of contacting an RGM inhibiting substance with an RGM expressing cell in a patient that has rheumatism, multiple sclerosis, Guillain-Barré syndrome, neuro-Behcet's disease, malignant anemia, type I (insulin-dependent) diabetes, systemic lupus erythematosus (SLE), inflammatory bowel disease (IBD), Sjogren's syndrome, atopic dermatitis, Goodpasture's syndrome, Graves' disease, autoimmune hemolytic anemia, autoimmune thrombocytopenic purpura, glomerulonephritis, myasthenia gravis, or Hashimoto's disease,
   wherein the RGM inhibiting substance is an anti-RGM neutralizing antibody or an RGM siRNA,
   thereby inhibiting activation of a T cell by the RGM expressing cell.

2. The method of inhibiting activation of a T cell according to claim 1, wherein the RGM inhibiting substance is an anti-RGM neutralizing antibody.

3. The method of inhibiting activation of a T cell according to claim 1, wherein the RGM inhibiting substance is an RGM siRNA.

4. The method of inhibiting activation of a T cell according to claim 1, wherein the patient has rheumatism.

5. The method of inhibiting activation of a T cell according to claim 1, wherein the patient has multiple sclerosis.

6. The method of inhibiting activation of a T cell according to claim 1, wherein the patient has Guillain-Barré syndrome.

7. The method of inhibiting activation of a T cell according to claim 1, wherein the patient has neuro-Behcet's disease.

8. The method of inhibiting activation of a T cell according to claim 1, wherein the patient has malignant anemia.

9. The method of inhibiting activation of a T cell according to claim 1, wherein the patient has type I (insulin-dependent) diabetes.

10. The method of inhibiting activation of a T cell according to claim 1, wherein the patient has systemic lupus erythematosus (SLE).

11. The method of inhibiting activation of a T cell according to claim 1, wherein the patient has inflammatory bowel disease (IBD).

12. The method of inhibiting activation of a T cell according to claim 1, wherein the patient has Sjogren's syndrome.

13. The method of inhibiting activation of a T cell according to claim 1, wherein the patient has atopic dermatitis.

14. The method of inhibiting activation of a T cell according to claim 1, wherein the patient has Goodpasture's syndrome.

15. The method of inhibiting activation of a T cell according to claim 1, wherein the patient has Graves' disease.

16. The method of inhibiting activation of a T cell according to claim 1, wherein the patient has autoimmune hemolytic anemia.

17. The method of inhibiting activation of a T cell according to claim 1, wherein the patient has autoimmune thrombocytopenic purpura.

18. The method of inhibiting activation of a T cell according to claim 1, wherein the patient has glomerulonephritis.

19. The method of inhibiting activation of a T cell according to claim 1, wherein the patient has myasthenia gravis.

20. The method of inhibiting activation of a T cell according to claim 1, wherein the patient has Hashimoto's disease.

\* \* \* \* \*